United States Patent [19]

Zombik et al.

[11] Patent Number: 5,066,673
[45] Date of Patent: Nov. 19, 1991

[54] SUBSTITUTED BENZYL 2-PHENYL-1-ALK(EN)YLCYCLOPROPANE-CARBOXYLATES AND THE USE THEREOF FOR CONTROLLING PESTS

[75] Inventors: Winfried Zombik, Ilvesheim; Hans Theobald, Limburgerhof; Bernd Wolf, Fussgoenheim; Ludwig Schuster, Limburgerhof; Peter Hofmeister, Neustadt; Christoph Kuenast, Otterstadt, all of Fed. Rep. of Germany

[73] Assignee: BASF Aktiengesellschaft, Ludwigshafen, Fed. Rep. of Germany

[21] Appl. No.: 482,890

[22] Filed: Feb. 22, 1990

[30] Foreign Application Priority Data

Mar. 4, 1989 [DE] Fed. Rep. of Germany ....... 3907069

[51] Int. Cl.$^5$ ................ C07C 255/31; C07C 69/743; A01N 37/08
[52] U.S. Cl. .................... 514/521; 514/531; 549/362; 549/442; 549/447; 558/407; 560/65; 560/8
[58] Field of Search .............. 560/65, 8; 558/407; 514/521, 531

[56] References Cited

U.S. PATENT DOCUMENTS

| 4,276,306 | 6/1981 | Fuchs et al. | 424/304 |
| 4,332,815 | 6/1982 | Engel | 424/274 |
| 4,344,963 | 8/1982 | Fuchs et al. | 560/8 X |
| 4,485,252 | 11/1984 | Fuchs et al. | 560/8 |
| 4,536,591 | 8/1985 | Plummer | 560/8 |
| 4,611,009 | 9/1986 | Fuchs et al. | 514/521 |

FOREIGN PATENT DOCUMENTS

| 0003336 | 6/1979 | European Pat. Off. . |
| 0049977 | 4/1982 | European Pat. Off. . |
| 0143152 | 6/1985 | European Pat. Off. . |

Primary Examiner—Joseph Paul Brust
Attorney, Agent, or Firm—Keil & Weinkauf

[57] ABSTRACT

Substituted benzyl 2-phenylalk(en)-1-ylcyclopropanecarboxylates of the general formula I

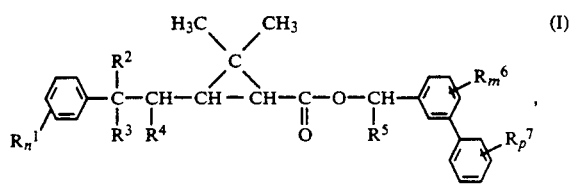

where
R$^1$ is halogen or in each case low molecular weight, alkyl, alkoxy, haloalkyl or haloalkoxy (n=1 to 5),
R$^2$ is halogen or, in each case low molecular weight, alkyl or haloalkyl,
R$^3$, R$^4$ are halogen or each is an electron in a double bond formed by them together,
R$^5$ is hydrogen or, in each case low molecular weight, alkyl, alkenyl, alkynyl or cyano,
R$^6$ is halogen or alkyl (n=1 to 4),
R$^7$ is halogen (p=0 to 25),
and their use for combating pests.

5 Claims, No Drawings

SUBSTITUTED BENZYL 2-PHENYL-1-ALK(EN)YLCYCLOPROPANE-CARBOXYLATES AND THE USE THEREOF FOR CONTROLLING PESTS

The present invention relates to novel benzyl 2-phenyl-1-alk(en)ylcyclopropanecarboxylates of the general formula I

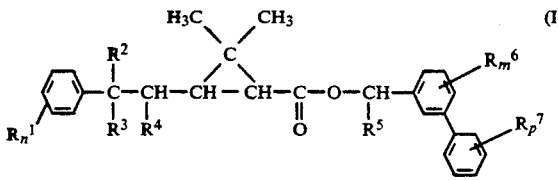

where
- $R^1$ is halogen or, in each case low molecular weight, alkyl, alkoxy, haloalkyl or haloalkoxy,
- $R^2$ is halogen or, in each case low molecular weight, alkyl or haloalkyl,
- $R^3$ and $R^4$ are halogen or each is an electron in a double bond formed by them together,
- $R^5$ is hydrogen or, in each case low molecular weight, alkyl, alkenyl or alkynyl, or cyano,
- $R^6$ is halogen or alkyl,
- R is halogen,
- n is 1 to 5,
- m is 1 to 4,
- p is 0 to 5.

The present invention also relates to pest-control agents which contain the cyclopropanecarboxylic esters I as active ingredients, and to methods for controlling pests with these active ingredients.

It has been disclosed that certains esters of 3-(2-phenylethenyl)-2,2-dimethylcyclopropanecarboxylic acid and alcohols which have a phenoxybenzyl or phenylbenzyl structure have insecticidal properties (cf., for example U.S. Pat. No. 4,536,591, EP 49,977, U.S. Pat. No. 4,332,815, EP 143,152, DE 2,730,515, DE 2,920,947 and EP 03,336).

However, the insecticidal action of these esters is in most cases unsatisfactory under certain conditions, e.g. low application rates or action on certain pests. Accordingly, the object was to prepare substituted benzyl cyclopropanecarboxylates with improved actions.

We have accordingly found that this object is achieved by the benzyl 2-phenyl-1-alk(en)ylcyclopropanecarboxylates I. Pest-control agents containing this active ingredient have a strong insecticidal and acaricidal action.

Unless stated otherwise, the following terms have the following preferred meanings in formula I:

For $R^1$

Halogen is fluorine, chlorine or bromine;

Alkyl is a straight or branched alkyl of 1 to 6, in particular 1 to 4, carbons, for example, methyl, ethyl, propyl, 1-methylethyl, butyl, 2-butyl, 2-methylpropyl, 1,1-dimethylethyl, 1,1-dimethylpropyl and 2,2-dimethylpropyl;

Alkoxy is a straight or branched alkyl of 1 to 6 carbons which is linked via oxygen to the phenyl or is a straight or branched alkyl which can be α,ω-linked via 2 oxygens, for example methoxy, ethoxy, propoxy, 2-propoxy, 2-methylpropoxy, butoxy, 2-butoxy, 2,2-dimethylethoxy, methylenedioxy, dimethylmethylenedioxy and 1,2-ethylenedioxy;

Haloalkyl is a straight or branched chain of 1 to 4 carbons which is substituted by 1 to 2n+1 halogens, where n is the number of carbons in the chain. Examples are trifluoromethyl, trichloromethyl, tribromomethyl, difluorochloromethyl, difluoromethyl, pentafluoroethyl, pentachloroethyl, 1,1,2,2-tetrafluoroethyl, 1,2,2-trifluoro-1,2-dichloroethyl and 1-trifluoromethyl-2,2,2-trifluoroethyl;

Haloalkoxy is a straight or branched chain of 1 to 6 carbons which is linked via oxygen to the phenyl and is substituted by 1 to 2n+1 halogens, where n is the number of carbons in the chain, or is a straight or branched alkyl of 1 to 6 carbons which can be linked via 2 oxygen atoms and is substituted by 1 to 2n+1 halogens, where n is the number of carbons in the chain. Examples are trifluoromethoxy, 1,1,2,2-tetrafluoroethoxy, 1,1,2,2,2-pentafluoroethoxy, 2,2,2-trichloroethoxy, 1-trifluoromethyl-2,2,2-trifluoroethoxy, difluoromethylene dioxy and bis(trifluoromethyl)methylenedioxy.

For $R^2$

Halogen is fluorine, chlorine, bromine and iodine;

Alkyl is a straight or branched chain of 1 to 4 carbons, for example methyl, ethyl, propyl and 1-methylethyl;

Haloalkyl is as specified for $R^1$;

For $R^3$ and $R^4$

Halogen is chlorine, bromine and iodine; and "each is an electron in a double bond formed by them together" means a $\pi$ bond between the two carbons to which $R^3$ and $R^4$ are assigned as substituents.

For $R^5$

Alkyl is a straight or branched chain of 1 to 4 carbons, for example methyl and ethyl.

Alkenyl is a straight or branched chain of 2 to 5 carbons with 1 or 2 double bonds, for example vinyl, 1-propenyl, 2-propenyl, alkenyl and 1,3-butadienyl;

Alkynyl is a straight or branched chain of 2 to 5, in particular 2 or 3, carbons with 1 or 2 triple bonds, for example ethynyl, 1-propynyl and 2-propynyl.

For $R^6$

Halogen is fluorine, chlorine and bromine and Alkyl is as specified for $R^5$.

For $R^7$ halogen is fluorine and chlorine.

n is an integer from 1 to 5, in particular 1 to 3.

m is an integer from 1 to 4, in particular 1 or 2.

p is 0 or an integer from 1 to 5, in particular 0, 1 or 2.

The esters of the general formula I can be obtained in a conventional manner by reacting cyclopropanecarboxylic acids IIa or derivatives thereof, such as chlorides, anhydrides or the like, in which $R^8$ is a conventional leaving group such as halogen, or is OM where M is an alkali metal or alkaline earth metal such as sodium, potassium, lithium, calcium or magnesium, with benzyl alcohols of the general formula IIIa or derivatives thereof, where $R^9$ is a conventional leaving group or is OM as defined above. Examples of conventional leaving groups are chlorine, bromine, iodine, O-mesyl, O-tosyl or a fluorinated alkanesulfonyl or arenesulfonyl.

The reaction starting from cyclopropanecarboxylic acid IIa ($R^8$=OH) and the benzyl alcohol IIIa ($R^9$=OH) is depicted in the following diagram:

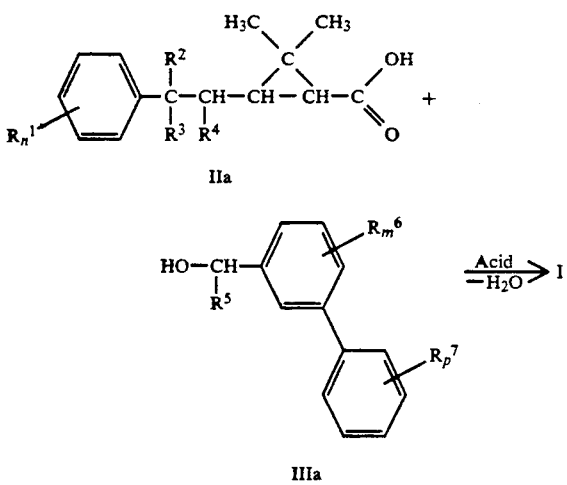

The rate of the esterification can be increased in a conventional manner by adding catalysts such as sulfuric acid, hydrogen halide, sulfonic acid or acid ion exchangers, and the esterification equilibrium can be displaced in the desired direction by removing the water or the ester I from the reaction mixture, e.g. by azeotropic distillation or by binding the water to sulfuric or hydrohalic acid.

It is equally possible to react the appropriate acid chlorides with the alcohols of the formula IIIa in the presence of an acid acceptor (cf. Houben-Weyl, Methoden der org. Chemie, Volume VIII, pp. 541 et seq., Georg-Thieme-Verlag, Stuttgart 1952).

Suitable acid-binding agents are the conventional basic agents, in particular aliphatic, aromatic and heterocyclic amines, e.g. triethylamine, dimethylamine, piperidine, dimethylaniline, dimethylbenzylamine, pyridine and 2-picoline.

The reaction can be carried out in a solvent or diluent. Suitable for this are the specified acid acceptors themselves or, for example, the following solvents or diluents or mixtures thereof: aliphatic and aromatic, possibly chlorinated hydrocarbons such as petroleum ether, benzene, toluene, xylene, naphtha, dichloromethane, chloroform, tetrachloromethane, 1,2-dichloroethane and chlorobenzene; ethers such as diethyl and di-n-butyl ether, methyl tert-butyl ether, tetrahydrofuran and dioxane; ketones, for example acetone, methyl ethyl ketone and methyl isopropyl ketone; and nitriles such as acetonitrile and propionitrile.

The starting materials are normally used in the stoichiometric ratio. However, an excess of one or other of them may be advantageous in some cases.

The rate of the reaction above 0° C. is adequate. Since the reaction usually evolves heat, it may be advantageous to provide means for cooling.

In some cases it is worthwhile and advantageous to esterify the compounds of the formula II in situ, especially when $R^5$ is cyano.

The esters according to the invention can also be prepared by virtually all conventional processes of ester synthesis, for example by reacting appropriate anhydrides with the alcohols of the formula IIIa, by reacting appropriate carboxylic salts with derivatives of the alcohols of the formula IIIa or by transesterification (cf. Houben-Weyl, loc. cit., pp. 508–628).

It is obvious that each of the compounds of the formula I occurs in the form of pure diastereomers, at least one pair of optical antipodes and, in many cases, in the form of multiple diastereomers, and can be used as active ingredients which, depending on the starting materials and the reaction conditions, are in pure form or as mixtures. In some cases their biological action depends on their steric configuration.

Individual stereoisomers of the carboxylic esters of claim 1 can be obtained by employing stereoisomerically pure starting compounds or by fractionating resulting product mixtures into their sterically pure constituents by conventional processes such as preparative TLC, column chromatography, MPLC or HPLC using suitable absorbents such as silica gel or alumina or other commercial absorbents and suitable solvents singly or in a mixture, for example petroleum ether, pentane, hexane, cyclohexane, diethyl ether, methyl tert-butyl ether, diisoproyl ether, toluene, benzene, acetone, methanol, ethanol, ethyl acetate, methylene chloride, chloroform or acetonitrile.

Processes for the preparation of the pyrethroid acids and derivatives thereof which are employed are described, for example, in Wegler, Chemie der Pflanzenschutz- und Schädlingsbekämpfungsmittel, Volume 7, pp. 57–66 and 137–172, Springer Verlag, Berlin, Heidelberg, New York 1981; Angew. Chem. Int. Ed. Engl. 20 (1981) 703–722; DE 2,738,150; DE 2,920,947; DE 2,916,357; EP 0,095,047.

Processes for the preparation of the alcohols of the general formula III which are employed, when $R^5$=hydrogen and $R^9$=OH or bromine, are described, for example, in Pest. Sci. 14, (1983) 560–570.

Compounds of the general formula IV can be prepared from compounds of the general formula III in which $R^9$ is OH by oxidation by literature methods (Houben-Weyl, Methoden der Org. Chemie, Volume E 3, pp. 275–299). It is likewise possible to prepare the latter from compounds of the general formula III in which $R^9$ is chlorine or bromine or $OSO_2$-p-toluene by literature methods (Houben-Weyl, Methoden der Org. Chemie, Volume E 3, pp. 248–265).

In addition, the benzyl halides of the formula III ($R^9$=Cl, Br) can be converted into benzyl alcohols of the formula III ($R^9$=OH) by literature methods (Houben-Weyl, Methoden der Org. Chemie, Volume 6/1a/1, pp. 174–223) and subsequently into compounds of the formula IV.

Compounds of the general formula III in which $R^5$ is alkyl, alkenyl or alkynyl and $R^9$ is OH may be prepared from compounds of the general formula IV by organometallic reactions in accordance with literature methods (Houben-Weyl, Methoden der Org. Chemie, Vol. 6/1a/2).

The compounds according to the invention are prepared in accordance with the disclosure and the following examples or appropriate modifications thereof.

The benzyl cyclopropanecarboxylates of the formula I are suitable for effectively combating pests such as insects, arachnids and nematodes. They may be used as pesticides in crop protection and in the hygiene, stores protection and veterinary sector.

Examples of injurious insects belonging to the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Dia-*

*phania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

Examples from the Coleoptera order are *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria.*

Examples from the Diptera order are *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

Examples from the Thysanoptera order are *Frankliniella fusca, Frankliniella occidentalis, Frankliniella tritici, Scirtothrips citri, Thrips oryzae, Thrips palmi* and *Thrips tabaci.*

Examples from the Hymenoptera order are *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

Examples from the Heteroptera order are *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

Examples from the Homoptera order are *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii.*

Examples from the Isoptera order are *Calotermes flavicollis, Leucotermes flavipes, Reticulitermes lucifugus* and *Termes natalensis.*

Examples from the Orthoptera order are *Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus.*

Examples from the Acarina order are *Amblyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae.*

Examples from the nematodes class are root-knot nematodes, e.g., *Meloidogyne hapla, Meloidogyne incognita* and *Meloidogyne javanica,* cyst-forming nematodes, e.g., *Globodera rostochiensis, Heterodera avenae, Hetrodera glycinae, Heterodera schachtii* and *Heterodera trifolii,* and stem and leaf eelworms, e.g., *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 1.1 is intimately mixed with 95 parts by weight of particulate kaolin. A dust is obtained containing 5% by weight of the active ingredient.

II. 30 parts by weight of compound no. 1.2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 1.5 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 1.7 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 1.1 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The active ingredient concentrations in the finished formulations may vary over a wide range. Generally, they are from 0.0001 to 10, and preferably from 0.01 to 1, %.

The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.01 to 10, particularly from 0.05 to 2, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

MANUFACTURING EXAMPLES

A)

trans,Z-3-[2-chloro-2-(4-chlorophenyl)-ethenyl]-2,2-dimethylcyclopropylcarboxylic chloride 174 g (0.22 mol) of anhydrous pyridine is added to a solution of 57 g (0.2 mol) of the appropriate carboxylic acid in 400 ml of anhydrous toluene. At 0° to 5° C., 59.5 g (0.5 mol) of thionyl chloride is dripped in and the whole is stirred for about 24 hours at room temperature. The precipitate is filtered off and the filtrate is evaporated down under reduced pressure. The oil which is obtained is taken up in methyl tert-butyl ether, cooled to 0° C., and the precipitate which forms is filtered off. The filtrate is evaporated down under reduced pressure, and the oil is dissolved in pentane/methyl tert-butyl ether (2/1), cooled to 0° C., and any precipitate which may have formed is filtered off. The filtrate is concentrated. The oil obtained (60 g=98.8% of theory) is sufficiently pure to be used for esterification.

250 MHz $^1$H-NMR spectrum in $CDCl_3$: δ [ppm]=s 1.33 (3H); s 1.41 (3H); d 2.28 I=6.7 Hz (1H); dd 2.74 I=8.3 and 6.7 Hz (1H); d 5.86 I=8.3 Hz (1H); d (broad) 7.31 I=8 Hz (2H); d (broad) 7.5 I=8 Hz (2H).

B)

trans,Z-2'-methyl-3'-phenylbenzyl-3-[2-chloro-2-(4-chlorophenyl)ethenyl]-2,2-dimethylcyclopropanecarboxylate 0.87 g (0.011 mol) of anhydrous pyridine is added to 1.98 g (0.01 mol) of 2-methyl-3-phenylbenzyl alcohol in 20 ml of anhydrous toluene. At room temperature, 3.035 g (0.01 mol) of the acyl chloride obtained under A), dissolved in 10 ml of anhydrous toluene, is dripped in. The mixture is stirred for about 18 hours at room temperature. About 100 ml of water is added to the reaction mixture, the organic phase is separated and the aqueous phase is thoroughly extracted several times with methyl tert-butyl ether. The combined organic phases are washed first with about 2N hydrochloric acid, then with water and then with saturated sodium chloride solution, and subsequently dried over sodium sulfate. After removal of the solvent under reduced pressure, 4.2 g of a yellow viscous oil is obtained. Purification by column chromatography on silica gel (230–400 mesh) using a 1:2 mixture of toluene/cyclohexane gives 3.9 g (84% of theory) of a pale yellow oil.

250 MHz $^1$H-NMR spectrum in CDCl$_3$: δ [ppm]=s 1.25 (3H); s 1.39 (3H); d 1.78 I=6.7 Hz (1H); s 2.26 (3H); dd 2.59 I=8.3 and 6.7 Hz (1H); s 2.5 (2H); d 5.84 I=8.3 Hz (1H); m 7.2–7.52 (12H).

The esters according to the invention of the general formula Ia ($R^3+R^4=$II bond) given in Table 1 and the esters of the general formula Ib ($R^3$, $R^4=$halogen) given in Table 2 for which physical data are given were prepared in accordance with the methods described; the remaining compounds in the tables may be obtained analogously, using corresponding starting materials.

TABLE 1

Compounds of the structure Ia

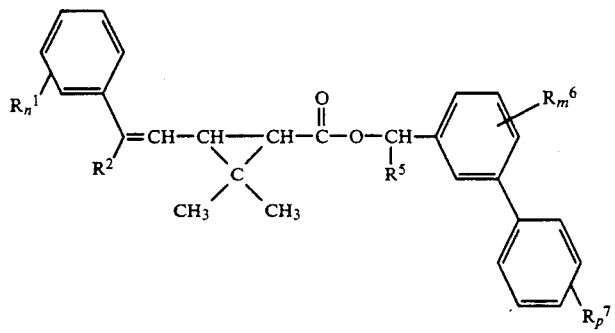

| Compound No. | $R_n^1$ | $R^2$ | $R^5$ | $R_m^6$ | $R_p^7$ | Configuration | Physical data $^1$H-NMR/δ[ppm]/CDCl$_3$ |
|---|---|---|---|---|---|---|---|
| 1.2 | 4-CF$_3$ | Cl | H | 2-CH$_3$ | H | trans/Z | s 1.25 (3H); s 1.40 (3H); d 1.80 I=6.7Hz (1H); s 2.25 (3H); dd 2.6 I=8.3 and 6.7Hz (1H); s 5.26 (2H); d 5.97 I=8.3Hz; m 7.2–7.48 (8H); m 7.53–7.72 (4H). |
| 1.3 | 4-CF$_3$ | Cl | H | 2-CH$_3$ | H | trans/E | s 1.23 (3H); s 1.26 (3H); d 1.70 I=6.7Hz (1H); dd 2.12 I=8.8 and 6.7Hz (1H); s 2.23 (3H); s 5.2 (2H); d 5.83 I=8.8Hz (1H); m 7.15–7.26 (8H); m 7.51–7.68 (4H). |
| 1.4 | 4-CF$_3$ | Cl | H | 2-CH$_3$ | H | | |
| 1.5 | 4-CF$_3$ | Cl | H | 2-CH$_3$ | H | cis/E | s 1.16 (3H); s 1.37 (3H); m 1.73–1.86 (2H); s 2.24 (3H); s 5.23 (2H); dd 6.48 I=7.5 and 2Hz (1H); m 7.1–7.46 (8H); m 7.5–7.7 (4H). |
| 1.6 | 4-CF$_3$ | Cl | CN | 2-CH$_3$ | H | trans/Z | A: s 1.26 (3H); s 1.36 (3H); d 1.83 I=4.2Hz (1H); s 2.3 (3H); dd 2.68 I=8.3 and 4.2Hz (1H); d 5.96 I=8.3Hz (1H); s 6.66 (1H); B: s 1.33 (3H); s 1.44 (3H); d 1.8 I=4.2Hz (1H); s 2.33 (3H); dd 2.62 I=8.3 and 4.2Hz (1H); d 5.95 I=8.3Hz (1H); s 6.68 (1H); A and B: m 7.21–7.5 (8H); m 7.53–7.72 (4H). |
| 1.7 | 4-CF$_3$ | Cl | CN | 2-CH$_3$ | H | trans/E | A: s 1.2 (3H); s 1.26 (3H); d 1.7 I=6.7Hz (1H); dd 2.18 I=9.1 and 6.7Hz (1H); s 2.23 (3H); d 5.83 I=9.1Hz (1H); s 6.56 (1H); B: s 1.28 (3H); s 1.31 (3H); d 1.73 I=6.7Hz (1H); dd 2.1 I=9.1 and 6.7Hz (1H); s 2.27 (3H); d 5.79 I=9.1Hz (1H); s 6.6 (1H); A and B: m 7.2–7.7 (12H). |
| 1.8 | 4-CF$_3$ | Cl | CN | 2-CH$_3$ | H | cis/Z | |
| 1.9 | 4-CF$_3$ | Cl | CN | 2-CH$_3$ | H | cis/E | |
| 1.10 | 4-CF$_3$ | Cl | C≡CH | 2-CH$_3$ | H | trans/Z | |
| 1.11 | 4-CF$_3$ | Cl | C≡CH | 2-CH$_3$ | H | trans/E | |
| 1.12 | 4-CF$_3$ | Cl | C≡CH | 2-CH$_3$ | H | cis/Z | |
| 1.13 | 4-CF$_3$ | Cl | C≡CH | 2-CH$_3$ | H | cis/E | |
| 1.14 | 4-CF$_3$ | Cl | CH=CH$_2$ | 2-CH$_3$ | H | | |

TABLE 1-continued

Compounds of the structure Ia

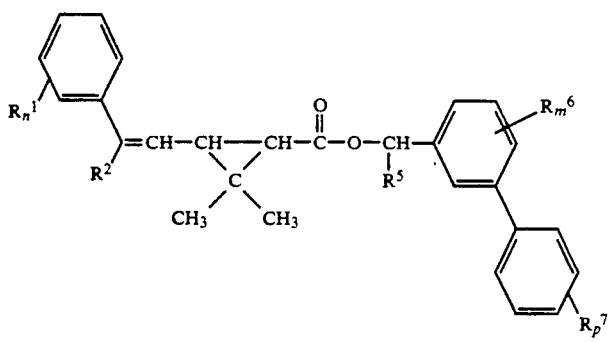

| Compound No. | $R_n^1$ | $R^2$ | $R^5$ | $R_m^6$ | $R_p^7$ | Configuration | Physical data $^1$H-NMR/δ[ppm]/CDCl$_3$ |
|---|---|---|---|---|---|---|---|
| 1.15 | 3-CF$_3$ | Cl | H | 2-CH$_3$ | H | | |
| 1.16 | 3-CF$_3$ | Cl | CN | 2-CH$_3$ | H | | |
| 1.17 | 3-CF$_3$ | Cl | C≡CH | 2-CH$_3$ | H | | |
| 1.18 | 3-CF$_3$ | Cl | CH=CH$_2$ | 2-CH$_3$ | H | | |
| 1.19 | 2-CF$_3$ | Cl | H | 2-CH$_3$ | H | | |
| 1.20 | 2-CF$_3$ | Cl | CN | 2-CH$_3$ | H | | |
| 1.21 | 2-CF$_3$ | Cl | C≡CH | 2-CH$_3$ | H | | |
| 1.22 | 2-CF$_3$ | Cl | CH=CH$_2$ | 2-CH$_3$ | H | | |
| 1.23 | 4-CF$_3$ | Br | H | 2-CH$_3$ | H | | |
| 1.24 | 3-CF$_3$ | Br | H | 2-CH$_3$ | H | | |
| 1.25 | 2-CF$_3$ | Br | H | 2-CH$_3$ | H | | |
| 1.26 | 4-CF$_3$ | F | H | 2-CH$_3$ | H | | |
| 1.27 | 4-CF$_3$ | F | CN | 2-CH$_3$ | H | | |
| 1.28 | 4-CF$_3$ | F | C≡CH | 2-CH$_3$ | H | | |
| 1.29 | 4-CF$_3$ | F | CH=CH$_2$ | 2-CH$_3$ | H | | |
| 1.30 | 3-CF$_3$ | F | H | 2-CH$_3$ | H | | |
| 1.31 | 2-CF$_3$ | F | H | 2-CH$_3$ | H | | |
| 1.32 | 4-CF$_3$ | CH$_3$ | H | 2-CH$_3$ | H | | |
| 1.33 | 3-CF$_3$ | CH$_3$ | H | 2-CH$_3$ | H | | |
| 1.34 | 2-CF$_3$ | CH$_3$ | H | 2-CH$_3$ | H | | |
| 1.35 | 4-CF$_3$ | CF$_3$ | H | 2-CH$_3$ | H | | |
| 1.36 | 3-CF$_3$ | CF$_3$ | H | 2-CH$_3$ | H | | |
| 1.37 | 2-CF$_3$ | CF$_3$ | H | 2-CH$_3$ | H | | |
| 1.38 | 4-CH$_3$ | Cl | H | 2-CH$_3$ | H | | |
| 1.39 | 4-CH$_3$ | Cl | CN | 2-CH$_3$ | H | | |
| 1.40 | 4-CH$_3$ | Cl | C≡CH | 2-CH$_3$ | H | | |
| 1.41 | 4-t-C$_4$H$_9$ | Cl | H | 2-CH$_3$ | H | | |
| 1.42 | 4-t-C$_4$H$_9$ | Cl | C≡CH | 2-CH$_3$ | H | | |
| 1.43 | 4-t-C$_4$H$_9$ | Cl | CN | 2-CH$_3$ | H | | |
| 1.44 | 4-CH$_3$ | F | H | 2-CH$_3$ | H | | |
| 1.45 | 4-CH$_3$ | Br | H | 2-CH$_3$ | H | | |
| 1.46 | 4-t-C$_4$H$_9$ | F | H | 2-CH$_3$ | H | | |
| 1.47 | 4-t-C$_4$H$_9$ | Br | H | 2-CH$_3$ | H | | |
| 1.48 | 4-t-C$_4$H$_9$ | CF$_3$ | H | 2-CH$_3$ | H | | |
| 1.49 | 4-t-C$_4$H$_9$ | CH$_3$ | H | 2-CH$_3$ | H | | |
| 1.50 | 4-OCH$_3$ | Cl | H | 2-CH$_3$ | H | | |
| 1.51 | 4-OCH$_3$ | Cl | CN | 2-CH$_3$ | H | | |
| 1.52 | 4-OCH$_3$ | Cl | C≡CH | 2-CH$_3$ | H | | |
| 1.53 | 4-OCH$_3$ | Br | H | 2-CH$_3$ | H | | |
| 1.54 | 4-OCH$_3$ | F | H | 2-CH$_3$ | H | | |
| 1.55 | 4-OCH$_3$ | CH$_3$ | H | 2-CH$_3$ | H | | |
| 1.56 | 4-OCH$_3$ | CF$_3$ | H | 2-CH$_3$ | H | | |
| 1.57 | 4-OC$_2$H$_5$ | Cl | H | 2-CH$_3$ | H | | |
| 1.58 | 4-OC$_2$H$_5$ | F | H | 2-CH$_3$ | H | | |
| 1.59 | 4-OC$_2$H$_5$ | Br | H | 2-CH$_3$ | H | | |
| 1.60 | 4-OC$_2$H$_5$ | Cl | CN | 2-CH$_3$ | H | | |
| 1.61 | 4-OC$_2$H$_5$ | Cl | C≡CH | 2-CH$_3$ | H | | |
| 1.62 | 4-OCF$_3$ | Cl | H | 2-CH$_3$ | H | | |
| 1.63 | 4-OCF$_3$ | Br | H | 2-CH$_3$ | H | | |
| 1.64 | 4-OCF$_3$ | F | H | 2-CH$_3$ | H | | |
| 1.65 | 4-OCF$_3$ | CH$_3$ | H | 2-CH$_3$ | H | | |
| 1.66 | 4-OCF$_3$ | CF$_3$ | H | 2-CH$_3$ | H | | |
| 1.67 | 4-OCF$_3$ | Cl | CN | 2-CH$_3$ | H | | |
| 1.68 | 4-OCF$_3$ | Cl | C≡CH | 2-CH$_3$ | H | | |
| 1.69 | 3-OCF$_3$ | Cl | H | 2-CH$_3$ | H | | |
| 1.70 | 2-OCF$_3$ | Cl | H | 2-CH$_3$ | H | | |
| 1.71 | 4-OCHF$_2$ | Cl | H | 2-CH$_3$ | H | | |
| 1.72 | 4-OCClF$_2$ | Cl | H | 2-CH$_3$ | H | | |
| 1.73 | 4-OCCl$_3$ | Cl | H | 2-CH$_3$ | H | | |

TABLE 1-continued

Compounds of the structure Ia

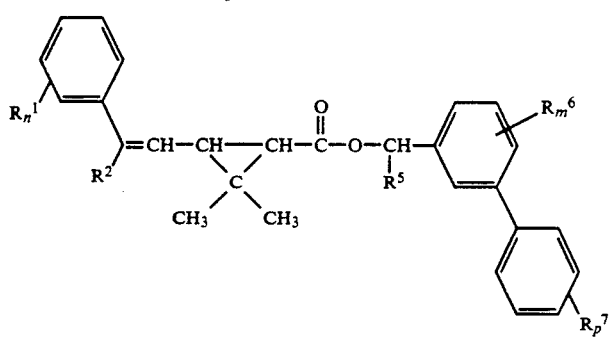

| Compound No. | $R_n^1$ | $R^2$ | $R^5$ | $R_m^6$ | $R_p^7$ | Configuration | Physical data $^1$H-NMR/δ[ppm]/CDCl$_3$ |
|---|---|---|---|---|---|---|---|
| 1.74 | 3,4- O\CH$_2$/O | Cl | H | 2-CH$_3$ | H | | |
| 1.75 | 3,4- O\CH$_2$/O | F | H | 2-CH$_3$ | H | | |
| 1.76 | 3,4- O\CH$_2$/O | Br | H | 2-CH$_3$ | H | | |
| 1.77 | 3,4- O\CH$_2$/O | CH$_3$ | H | 2-CH$_3$ | H | | |
| 1.78 | 3,4- O\CH$_2$/O | CF$_3$ | H | 2-CH$_3$ | H | | |
| 1.79 | 3,4- O\CH$_2$/O | Cl | CN | 2-CH$_3$ | H | | |
| 1.80 | 3,4- O\CH$_2$/O | Cl | C≡CH | 2-CH$_3$ | H | | |
| 1.81 | 3,4- O\CF$_2$/O | Cl | H | 2-CH$_3$ | H | | |
| 1.82 | 3,4- O\CF$_2$/O | Br | H | 2-CH$_3$ | H | | |
| 1.83 | 3,4- O\CF$_2$/O | F | H | 2-CH$_3$ | H | | |
| 1.84 | 3,4- O\CF$_2$/O | CH$_3$ | H | 2-CH$_3$ | H | | |

TABLE 1-continued

Compounds of the structure Ia

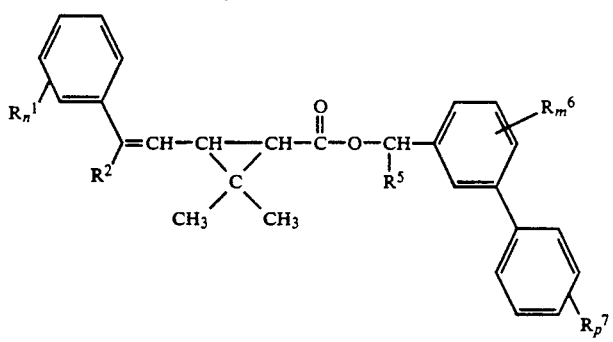

| Compound No. | $R_n^1$ | $R^2$ | $R^5$ | $R_m^6$ | $R_p^7$ | Configuration | Physical data $^1$H-NMR/δ[ppm]/CDCl$_3$ |
|---|---|---|---|---|---|---|---|
| 1.85 | 3,4-O-CF$_2$-O | CF$_3$ | H | 2-CH$_3$ | H | | |
| 1.86 | 3,4-O-CH$_2$-O-CH$_2$ | Cl | H | 2-CH$_3$ | H | | |
| 1.87 | 3,4-O-CH$_2$-O-CH$_2$ | Br | H | 2-CH$_3$ | H | | |
| 1.88 | 3,4-O-CF$_2$-O-CF$_2$ | Cl | H | 2-CH$_3$ | H | | |
| 1.89 | 4-F | Cl | H | 2-CH$_3$ | H | | |
| 1.90 | 4-F | Br | H | 2-CH$_3$ | H | | |
| 1.91 | 4-F | F | H | 2-CH$_3$ | H | | |
| 1.92 | 4-F | CH$_3$ | H | 2-CH$_3$ | H | | |
| 1.93 | 4-F | CF$_3$ | H | 2-CH$_3$ | H | | |
| 1.94 | 4-F | Cl | CN | 2-CH$_3$ | H | | |
| 1.95 | 4-F | Cl | C≡CH | 2-CH$_3$ | H | | |
| 1.96 | 3-F | Cl | H | 2-CH$_3$ | H | | |
| 1.97 | 2-F | Cl | H | 2-CH$_3$ | H | | |
| 1.98 | 3,4-F$_2$ | Cl | H | 2-CH$_3$ | H | | |
| 1.99 | 2,4-F$_2$ | Cl | H | 2-CH$_3$ | H | | |
| 1.100 | 2,3-F$_2$ | Cl | H | 2-CH$_3$ | H | | |
| 1.101 | penta F | Cl | H | 2-CH$_3$ | H | | |
| 1.102 | 4-Cl | Cl | H | 2-CH$_3$ | H | | |
| 1.103 | 4-Cl | Br | H | 2-CH$_3$ | H | | |
| 1.104 | 4-Cl | I | H | 2-CH$_3$ | H | | |
| 1.105 | 4-Cl | F | H | 2-CH$_3$ | H | | |
| 1.106 | 4-Cl | Cl | CN | 2-CH$_3$ | H | | |
| 1.107 | 4-Cl | Cl | C≡CH | 2-CH$_3$ | H | | |
| 1.108 | 2-Cl | Cl | H | 2-CH$_3$ | H | | |
| 1.109 | 3-Cl | Cl | H | 2-CH$_3$ | H | | |
| 1.110 | 2,4-Cl$_2$ | Cl | H | 2-CH$_3$ | H | | |
| 1.111 | 3,4-Cl$_2$ | Cl | H | 2-CH$_3$ | H | | |
| 1.112 | 2,3-Cl$_2$ | Cl | H | 2-CH$_3$ | H | | |
| 1.113 | penta Cl | Cl | H | 2-CH$_3$ | H | | |
| 1.114 | 4-Br | Cl | H | 2-CH$_3$ | H | | |
| 1.115 | 4-Br | Br | H | 2-CH$_3$ | H | | |
| 1.116 | 4-Br | F | H | 2-CH$_3$ | H | | |
| 1.117 | 4-Br | CF$_3$ | H | 2-CH$_3$ | H | | |
| 1.118 | 4-I | Cl | H | 2-CH$_3$ | H | | |
| 1.119 | 4-CF$_3$, 2-Cl | Cl | H | 2-CH$_3$ | H | | |
| 1.120 | 2-CF$_3$, 4-Cl | Cl | H | 2-CH$_3$ | H | | |
| 1.121 | 4-OC$_2$H$_5$, 3-Cl | Cl | H | 2-CH$_3$ | H | | |
| 1.122 | 4-OCF$_3$, 3-Cl | Cl | H | 2-CH$_3$ | H | | |
| 1.123 | 4-CF$_3$ | Cl | H | 2-CF$_3$ | H | | |
| 1.124 | 4-CF$_3$ | Br | H | 2-CF$_3$ | H | | |
| 1.125 | 4-CF$_3$ | F | H | 2-CF$_3$ | H | | |
| 1.126 | 4-CF$_3$ | Cl | CN | 2-CF$_3$ | H | | |
| 1.127 | 4-CF$_3$ | Cl | C≡CH | 2-CF$_3$ | H | | |
| 1.128 | 4-CF$_3$ | Cl | CH=CH$_2$ | 2-CF$_3$ | H | | |
| 1.129 | 4-CF$_3$ | CF$_3$ | H | 2-CF$_3$ | H | | |
| 1.130 | 4-CF$_3$ | CH$_3$ | H | 2-CF$_3$ | H | | |
| 1.131 | 4-Cl | Cl | H | 2-CF$_3$ | H | | |
| 1.132 | 4-Cl | Br | H | 2-CF$_3$ | H | | |

TABLE 1-continued

Compounds of the structure Ia

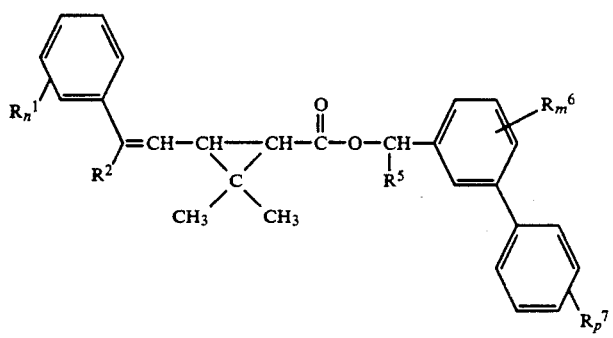

| Compound No. | $R_n^1$ | $R^2$ | $R^5$ | $R_m^6$ | $R_p^7$ | Configuration | Physical data $^1$H-NMR/δ[ppm]/CDCl$_3$ |
|---|---|---|---|---|---|---|---|
| 1.133 | 4-Cl | F | H | 2-CF$_3$ | H | | |
| 1.134 | 4-Cl | CF$_3$ | H | 2-CF$_3$ | H | | |
| 1.135 | 4-Cl | CH$_3$ | H | 2-CF$_3$ | H | | |
| 1.136 | 4-Cl | Cl | CN | 2-CF$_3$ | H | | |
| 1.137 | 4-Cl | Cl | C≡CH | 2-CF$_3$ | H | | |
| 1.138 | 4-Br | Cl | H | 2-CF$_3$ | H | | |
| 1.139 | 4-OCF$_3$ | Cl | H | 2-CF$_3$ | H | | |
| 1.140 | 4-OC$_2$H$_5$ | Cl | H | 2-CF$_3$ | H | | |
| 1.141 | 4-F | Cl | H | 2-CF$_3$ | H | | |
| 1.142 | 4-F | F | H | 2-CF$_3$ | H | | |
| 1.143 | 4-F | Br | H | 2-CF$_3$ | H | | |
| 1.144 | penta F | Cl | H | 2-CF$_3$ | H | | |
| 1.145 | penta Cl | Cl | H | 2-CF$_3$ | H | | |
| 1.146 | 4-CF$_3$, 2-Cl | Cl | H | 2-CF$_3$ | H | | |
| 1.147 | penta Cl | Br | H | 2-CF$_3$ | H | | |
| 1.148 | penta F | Br | H | 2-CF$_3$ | H | | |
| 1.149 | 4-CF$_3$ | Cl | H | 2-Cl | H | | |
| 1.150 | 4-CF$_3$ | Cl | CN | 2-Cl | H | | |
| 1.151 | 4-CF$_3$ | Cl | C≡CH | 2-Cl | H | | |
| 1.152 | 4-CF$_3$ | Br | H | 2-Cl | H | | |
| 1.153 | 4-CF$_3$ | F | H | 2-Cl | H | | |
| 1.154 | 4-CF$_3$ | CH$_3$ | H | 2-Cl | H | | |
| 1.155 | 4-CF$_3$ | CF$_3$ | H | 2-Cl | H | | |
| 1.156 | 4-Cl | Cl | H | 2-Cl | H | | |
| 1.157 | 4-Cl | Cl | CN | 2-Cl | H | | |
| 1.158 | 4-Cl | Cl | C≡CH | 2-Cl | H | | |
| 1.159 | 4-Cl | Br | H | 2-Cl | H | | |
| 1.160 | 4-Cl | F | H | 2-Cl | H | | |
| 1.161 | 4-Cl | CH$_3$ | H | 2-Cl | H | | |
| 1.162 | 4-Cl | CF$_3$ | H | 2-Cl | H | | |
| 1.163 | penta Cl | Cl | H | 2-Cl | H | | |
| 1.164 | penta Cl | Br | H | 2-Cl | H | | |
| 1.165 | 4-F | Cl | H | 2-Cl | H | | |
| 1.166 | 4-F | F | H | 2-Cl | H | | |
| 1.167 | 4-F | Br | H | 2-Cl | H | | |
| 1.168 | penta F | Cl | H | 2-Cl | H | | |
| 1.169 | penta F | Br | H | 2-Cl | H | | |
| 1.170 | 4-OCH$_3$ | Cl | H | 2-Cl | H | | |
| 1.171 | 4-OC$_2$H$_5$ | Cl | H | 2-Cl | H | | |
| 1.172 | 4-OCF$_3$ | Cl | H | 2-Cl | H | | |
| 1.173 | 4-CF$_3$, O—Cl | Cl | H | 2-Cl | H | | |
| 1.174 | 4-OC$_2$H$_5$, m-Cl | Cl | H | 2-Cl | H | | |
| 1.175 | 4-CF$_3$ | Cl | H | 2-F | H | | |
| 1.176 | 4-CF$_3$ | Br | H | 2-F | H | | |
| 1.177 | 4-CF$_3$ | F | H | 2-F | H | | |
| 1.178 | 4-CF$_3$ | CH$_3$ | H | 2-F | H | | |
| 1.179 | 4-CF$_3$ | CF$_3$ | H | 2-F | H | | |
| 1.180 | 4-Cl | Cl | H | 2-F | H | | |
| 1.181 | 4-Cl | Br | H | 2-F | H | | |
| 1.182 | 4-Cl | F | H | 2-F | H | | |
| 1.183 | 4-Cl | Me | H | 2-F | H | | |
| 1.184 | 4-Cl | CF$_3$ | H | 2-F | H | | |
| 1.185 | 4-Cl | Cl | CN | 2-F | H | | |
| 1.186 | 4-Cl | Cl | C≡CH | 2-F | H | | |
| 1.187 | penta Cl | Cl | H | 2-F | H | | |
| 1.188 | penta Cl | Br | H | 2-F | H | | |
| 1.189 | 4-F | Cl | H | 2-F | H | | |
| 1.190 | 4-F | Br | H | 2-F | H | | |
| 1.191 | 4-F | Me | H | 2-F | H | | |
| 1.192 | 4-F | CF$_3$ | H | 2-F | H | | |
| 1.193 | 4-OCH$_3$ | Cl | H | 2-F | H | | |
| 1.194 | 4-OC$_2$H$_5$ | Cl | H | 2-F | H | | |

TABLE 1-continued

Compounds of the structure Ia

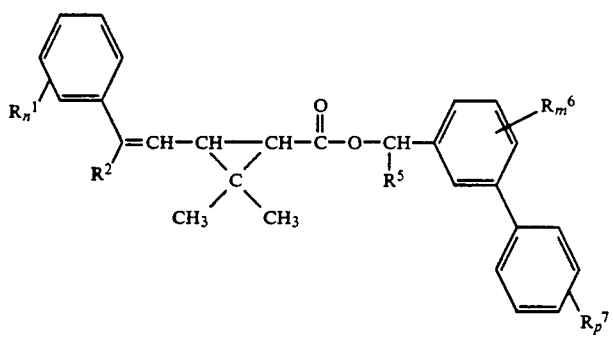

| Compound No. | $R_n^1$ | $R^2$ | $R^5$ | $R_m^6$ | $R_p^7$ | Configuration | Physical data $^1$H-NMR/δ[ppm]/CDCl$_3$ |
|---|---|---|---|---|---|---|---|
| 1.195 | 4-OCF$_3$ | Cl | H | 2-F | H | | |
| 1.196 | penta F | Cl | H | 2-F | H | | |
| 1.197 | penta F | Br | H | 2-F | H | | |
| 1.198 | 4-CF$_3$ | Cl | H | 2,4-Cl$_2$ | H | | |
| 1.199 | 4-CF$_3$ | Br | H | 2,4-Cl$_2$ | H | | |
| 1.200 | 4-CF$_3$ | Cl | CN | 2,4-Cl$_2$ | H | | |
| 1.201 | 4-CF$_3$ | Cl | C≡CH | 2,4-Cl$_2$ | H | | |
| 1.202 | 4-Cl | Cl | H | 2,4-Cl$_2$ | H | | |
| 1.203 | 4-Cl | Br | H | 2,4-Cl$_2$ | H | | |
| 1.204 | 4-Cl | F | H | 2,4-Cl$_2$ | H | | |
| 1.205 | 4-Cl | Cl | CN | 2,4-Cl$_2$ | H | | |
| 1.206 | 4-Cl | Cl | C≡CH | 2,4-Cl$_2$ | H | | |
| 1.207 | 4-Br | Cl | H | 2,4-Cl$_2$ | H | | |
| 1.208 | 4-Br | Br | H | 2,4-Cl$_2$ | H | | |
| 1.209 | 4-OCH$_3$ | Cl | H | 2,4-Cl$_2$ | H | | |
| 1.210 | 4-OC$_2$H$_5$ | Cl | H | 2,4-Cl$_2$ | H | | |
| 1.211 | 4-OCF$_3$ | Cl | H | 2,4-Cl$_2$ | H | | |
| 1.212 | 4-CH$_3$ | Cl | H | 2,4-Cl$_2$ | H | | |
| 1.213 | 4-t-C$_4$H$_9$ | Cl | H | 2,4-Cl$_2$ | H | | |
| 1.214 | 4-CF$_3$ | Cl | H | 2-CH$_3$, 4-F | H | | |
| 1.215 | 4-CF$_3$ | Br | H | 2-CH$_3$, 4-F | H | | |
| 1.216 | 4-CF$_3$ | F | H | 2-CH$_3$, 4-F | H | | |
| 1.217 | 4-CF$_3$ | Cl | CN | 2-CH$_3$, 4-F | H | | |
| 1.218 | 4-CF$_3$ | Cl | C≡CH | 2-CH$_3$, 4-F | H | | |
| 1.219 | 4-CF$_3$ | CH$_3$ | H | 2-CH$_3$, 4-F | H | | |
| 1.220 | 4-CF$_3$ | CF$_3$ | H | 2-CH$_3$, 4-F | H | | |
| 1.221 | 4-Cl | Cl | H | 2-CH$_3$, 4-F | H | | |
| 1.222 | 4-Cl | Br | H | 2-CH$_3$, 4-F | H | | |
| 1.223 | 4-Cl | F | H | 2-CH$_3$, 4-F | H | | |
| 1.224 | 4-Cl | Cl | CN | 2-CH$_3$, 4-F | H | | |
| 1.225 | 4-Cl | Cl | C≡CH | 2-CH$_3$, 4-F | H | | |
| 1.226 | 4-Cl | CH$_3$ | H | 2-CH$_3$, 4-F | H | | |
| 1.227 | 4-Cl | CF$_3$ | H | 2-CH$_3$, 4-F | H | | |
| 1.228 | 4-OCH$_3$ | Cl | H | 2-CH$_3$, 4-F | H | | |
| 1.229 | 4-OC$_2$H$_5$ | Cl | H | 2-CH$_3$, 4-F | H | | |
| 1.230 | 4-OCF$_3$ | Cl | H | 2-CH$_3$, 4-F | H | | |
| 1.231 | 4-CH$_3$ | Cl | H | 2-CH$_3$, 4-F | H | | |
| 1.232 | 4-t-C$_4$H$_9$ | Cl | H | 2-CH$_3$, 4-F | H | | |
| 1.234 | 4-CF$_3$ | Cl | H | 2-CH$_3$ | 4-F | | |
| 1.235 | 4-CF$_3$ | F | H | 2-CH$_3$ | 4-F | | |
| 1.236 | 4-CF$_3$ | Cl | CN | 2-CH$_3$ | 4-F | | |
| 1.237 | 4-CF$_3$ | Cl | C≡CH | 2-CH$_3$ | 4-F | | |
| 1.238 | 4-CF$_3$ | CH$_3$ | H | 2-CH$_3$ | 4-F | | |
| 1.239 | 4-CF$_3$ | CF$_3$ | H | 2-CH$_3$ | 4-F | | |
| 1.240 | 4-Cl | Cl | H | 2-CH$_3$ | 4-F | | |
| 1.241 | 4-Cl | Br | H | 2-CH$_3$ | 4-F | | |
| 1.242 | 4-Cl | F | H | 2-CH$_3$ | 4-F | | |
| 1.243 | 4-Cl | I | H | 2-CH$_3$ | 4-F | | |
| 1.244 | 4-Cl | Cl | CN | 2-CH$_3$ | 4-F | | |
| 1.245 | 4-Cl | Cl | C≡CH | 2-CH$_3$ | 4-F | | |
| 1.246 | 4-Cl | CH$_3$ | H | 2-CH$_3$ | 4-F | | |
| 1.247 | 4-Cl | CF$_3$ | H | 2-CH$_3$ | 4-F | | |
| 1.248 | 4-OCH$_3$ | Cl | H | 2-CH$_3$ | 4-F | | |
| 1.249 | 4-OC$_2$H$_5$ | Cl | H | 2-CH$_3$ | 4-F | | |
| 1.250 | 4-OCF$_3$ | Cl | H | 2-CH$_3$ | 4-F | | |
| 1.251 | 4-CH$_3$ | Cl | H | 2-CH$_3$ | 4-F | | |
| 1.252 | 4-t-C$_4$H$_9$ | Cl | H | 2-CH$_3$ | 4-F | | |
| 1.253 | 4-CF$_3$, 2-Cl | Cl | H | 2-CH$_3$ | 4-F | | |
| 1.254 | 4-Cl, 2-CF$_3$ | Cl | H | 2-CH$_3$ | 4-F | | |
| 1.255 | 4-CF$_3$ | Cl | H | 2-CH$_3$ | 2,4-F$_2$ | | |
| 1.256 | 4-CF$_3$ | Br | H | 2-CH$_3$ | 2,4-F$_2$ | | |
| 1.257 | 4-CF$_3$ | F | H | 2-CH$_3$ | 2,4-F$_2$ | | |

TABLE 1-continued

Compounds of the structure Ia

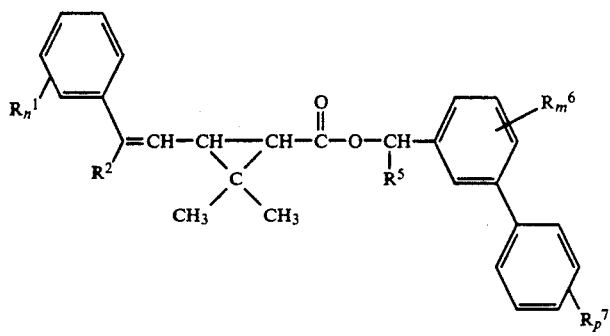

| Compound No. | $R_n^1$ | $R^2$ | $R^5$ | $R_m^6$ | $R_p^7$ | Configuration | Physical data $^1$H-NMR/δ[ppm]/CDCl$_3$ |
|---|---|---|---|---|---|---|---|
| 1.258 | 4-CF$_3$ | CH$_3$ | H | 2-CH$_3$ | 2,4-F$_2$ | | |
| 1.259 | 4-CF$_3$ | CF$_3$ | H | 2-CH$_3$ | 2,4-F$_2$ | | |
| 1.260 | 4-CF$_3$ | Cl | CN | 2-CH$_3$ | 2,4-F$_2$ | | |
| 1.261 | 4-CF$_3$ | Cl | C≡CH | 2-CH$_3$ | 2,4-F$_2$ | | |
| 1.262 | 4-Cl | Cl | H | 2-CH$_3$ | 2,4-F$_2$ | | |
| 1.263 | 4-Cl | Br | H | 2-CH$_3$ | 2,4-F$_2$ | | |
| 1.264 | 4-Cl | F | H | 2-CH$_3$ | 2,4-F$_2$ | | |
| 1.265 | 4-Cl | CH$_3$ | H | 2-CH$_3$ | 2,4-F$_2$ | | |
| 1.266 | 4-Cl | CF$_3$ | H | 2-CH$_3$ | 2,4-F$_2$ | | |
| 1.267 | 4-Cl | Cl | CN | 2-CH$_3$ | 2,4-F$_2$ | | |
| 1.268 | 4-Cl | Cl | C≡CH | 2-CH$_3$ | 2,4-F$_2$ | | |
| 1.269 | 4-OCH$_3$ | Cl | H | 2-CH$_3$ | 2,4-F$_2$ | | |
| 1.270 | 4-OC$_2$H$_5$ | Cl | H | 2-CH$_3$ | 2,4-F$_2$ | | |
| 1.271 | 4-OCF$_3$ | Cl | H | 2-CH$_3$ | 2,4-F$_2$ | | |
| 1.272 | 4-CH$_3$ | Cl | H | 2-CH$_3$ | 2,4-F$_2$ | | |
| 1.273 | 4-t-C$_4$H$_9$ | Cl | H | 2-CH$_3$ | 2,4-F$_2$ | | |
| 1.274 | 4-F | Cl | H | 2-CH$_3$ | 2,4-F$_2$ | | |
| 1.275 | 4-F | Cl | H | 2-CH$_3$ | 4-F | | |
| 1.276 | 4-F | Cl | H | 2-CH$_3$, 4-F | H | | |
| 1.277 | 4-CF$_3$ | Cl | H | 2-CH$_3$ | 3,4-F$_2$ | | |
| 1.278 | 4-CF$_3$ | Br | H | 2-CH$_3$ | 3,4-F$_2$ | | |
| 1.279 | 4-CF$_3$ | F | H | 2-CH$_3$ | 3,4-F$_2$ | | |
| 1.280 | 4-CF$_3$ | I | H | 2-CH$_3$ | 3,4-F$_2$ | | |
| 1.281 | 4-CF$_3$ | CH$_3$ | H | 2-CH$_3$ | 3,4-F$_2$ | | |
| 1.282 | 4-CF$_3$ | CF$_3$ | H | 2-CH$_3$ | 3,4-F$_2$ | | |
| 1.283 | 4-CF$_3$ | Cl | CN | 2-CH$_3$ | 3,4-F$_2$ | | |
| 1.284 | 4-CF$_3$ | Cl | C≡CH | 2-CH$_3$ | 3,4-F$_2$ | | |
| 1.285 | 4-Cl | Cl | H | 2-CH$_3$ | 3,4-F$_2$ | | |
| 1.286 | 4-Cl | Br | H | 2-CH$_3$ | 3,4-F$_2$ | | |
| 1.287 | 4-Cl | F | H | 2-CH$_3$ | 3,4-F$_2$ | | |
| 1.288 | 4-Cl | CH$_3$ | H | 2-CH$_3$ | 3,4-F$_2$ | | |
| 1.289 | 4-Cl | CF$_3$ | H | 2-CH$_3$ | 3,4-F$_2$ | | |
| 1.290 | 4-Cl | Cl | CN | 2-CH$_3$ | 3,4-F$_2$ | | |
| 1.291 | 4-Cl | Cl | C≡CH | 2-CH$_3$ | 3,4-F$_2$ | | |
| 1.292 | 4-OCH$_3$ | Cl | H | 2-CH$_3$ | 3,4-F$_2$ | | |
| 1.293 | 4-OC$_2$H$_5$ | Cl | H | 2-CH$_3$ | 3,4-F$_2$ | | |
| 1.294 | 4-OCF$_3$ | Cl | H | 2-CH$_3$ | 3,4-F$_2$ | | |
| 1.295 | 4-CH$_3$ | Cl | H | 2-CH$_3$ | 3,4-F$_2$ | | |
| 1.296 | 4-t-C$_4$H$_9$ | Cl | H | 2-CH$_3$ | 3,4-F$_2$ | | |
| 1.297 | 4-CF$_3$ | Cl | H | 2-CH$_3$ | 4-Cl | | |
| 1.298 | 4-CF$_3$ | Br | H | 2-CH$_3$ | 4-Cl | | |
| 1.299 | 4-CF$_3$ | F | H | 2-CH$_3$ | 4-Cl | | |
| 1.300 | 4-CF$_3$ | I | H | 2-CH$_3$ | 4-Cl | | |
| 1.301 | 4-CF$_3$ | CH$_3$ | H | 2-CH$_3$ | 4-Cl | | |
| 1.302 | 4-CF$_3$ | CF$_3$ | H | 2-CH$_3$ | 4-Cl | | |
| 1.303 | 4-CF$_3$ | Cl | CN | 2-CH$_3$ | 4-Cl | | |
| 1.304 | 4-CF$_3$ | Cl | C≡CH | 2-CH$_3$ | 4-Cl | | |
| 1.305 | 4-Cl | Cl | H | 2-CH$_3$ | 4-Cl | | |
| 1.306 | 4-Cl | Br | H | 2-CH$_3$ | 4-Cl | | |
| 1.307 | 4-Cl | I | H | 2-CH$_3$ | 4-Cl | | |
| 1.308 | 4-Cl | F | H | 2-CH$_3$ | 4-Cl | | |
| 1.309 | 4-Cl | CH$_3$ | H | 2-CH$_3$ | 4-Cl | | |
| 1.310 | 4-Cl | CF$_3$ | H | 2-CH$_3$ | 4-Cl | | |
| 1.311 | 4-Cl | Cl | CN | 2-CH$_3$ | 4-Cl | | |
| 1.312 | 4-Cl | Cl | C≡CH | 2-CH$_3$ | 4-Cl | | |
| 1.213 | 4-F | Cl | H | 2-CH$_3$ | 4-Cl | | |
| 1.314 | 4-F | Br | H | 2-CH$_3$ | 4-Cl | | |
| 1.315 | 4-OCH$_3$ | Cl | H | 2-CH$_3$ | 4-Cl | | |
| 1.316 | 4-OC$_2$H$_5$ | Cl | H | 2-CH$_3$ | 4-Cl | | |
| 1.317 | 4-OCF$_3$ | Cl | H | 2-CH$_3$ | 4-Cl | | |
| 1.318 | 4-CH$_3$ | Cl | H | 2-CH$_3$ | 4-Cl | | |
| 1.319 | 4-t-C$_4$H$_9$ | Cl | H | 2-CH$_3$ | 4-Cl | | |

TABLE 1-continued

Compounds of the structure Ia

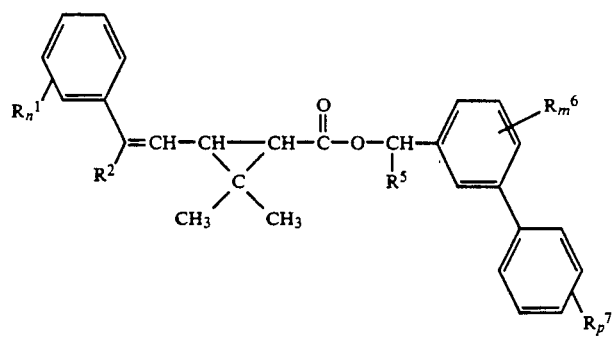

| Compound No. | $R_n^1$ | $R^2$ | $R^5$ | $R_m^6$ | $R_p^7$ | Configuration | Physical data $^1$H-NMR/$\delta$[ppm]/CDCl$_3$ |
|---|---|---|---|---|---|---|---|
| 1.320 | 4-CF$_3$ | Cl | H | tetra-F | H | | |
| 1.321 | 4-CF$_3$ | Br | H | tetra-F | H | | |
| 1.322 | 4-CF$_3$ | F | H | tetra-F | H | | |
| 1.323 | 4-CF$_3$ | I | H | tetra-F | H | | |
| 1.324 | 4-CF$_3$ | Cl | CN | tetra-F | H | | |
| 1.325 | 4-CF$_3$ | Cl | C≡CH | tetra-F | H | | |
| 1.336 | 4-Cl | Cl | H | tetra-F | H | | |
| 1.337 | 4-Cl | Br | H | tetra-F | H | | |
| 1.338 | 4-Cl | F | H | tetra-F | H | | |
| 1.339 | 4-Cl | I | H | tetra-F | H | | |
| 1.340 | 4-Cl | CH$_3$ | H | tetra-F | H | | |
| 1.341 | 4-Cl | CF$_3$ | H | tetra-F | H | | |
| 1.342 | 4-Cl | Cl | CN | tetra-F | H | | |
| 1.343 | 4-Cl | Cl | C≡CH | tetra-F | H | | |
| 1.344 | 4-F | Cl | H | tetra-F | H | | |
| 1.345 | 4-OCH$_3$ | Cl | H | tetra-F | H | | |
| 1.346 | 4-OC$_2$H$_5$ | Cl | H | tetra-F | H | | |
| 1.347 | 4-OCF$_3$ | Cl | H | tetra-F | H | | |
| 1.348 | 4-CH$_3$ | Cl | H | tetra-F | H | | |
| 1.349 | 4-t-C$_4$H$_9$ | Cl | H | tetra-F | H | | |
| 1.350 | 4-CF$_3$ | Cl | H | 2-CH$_3$ | penta-F | | |
| 1.351 | 4-CF$_3$ | Br | H | 2-CH$_3$ | penta-F | | |
| 1.352 | 4-CF$_3$ | F | H | 2-CH$_3$ | penta-F | | |
| 1.353 | 4-CF$_3$ | I | H | 2-CH$_3$ | penta-F | | |
| 1.354 | 4-CF$_3$ | CH$_3$ | H | 2-CH$_3$ | penta-F | | |
| 1.355 | 4-CF$_3$ | CF$_3$ | H | 2-CH$_3$ | penta-F | | |
| 1.356 | 4-CF$_3$ | Cl | CN | 2-CH$_3$ | penta-F | | |
| 1.357 | 4-CF$_3$ | Cl | C≡CH | 2-CH$_3$ | penta-F | | |
| 1.358 | 4-Cl | Cl | H | 2-CH$_3$ | penta-F | | |
| 1.359 | 4-Cl | Br | H | 2-CH$_3$ | penta-F | | |
| 1.360 | 4-Cl | F | H | 2-CH$_3$ | penta-F | | |
| 1.361 | 4-Cl | I | H | 2-CH$_3$ | penta-F | | |
| 1.362 | 4-Cl | CH$_3$ | H | 2-CH$_3$ | penta-F | | |
| 1.363 | 4-Cl | CF$_3$ | H | 2-CH$_3$ | penta-F | | |
| 1.364 | 4-Cl | Cl | CN | 2-CH$_3$ | penta-F | | |
| 1.365 | 4-Cl | Cl | C≡CH | 2-CH$_3$ | penta-F | | |
| 1.366 | 4-F | Cl | H | 2-CH$_3$ | penta-F | | |
| 1.367 | 4-OCH$_3$ | Cl | H | 2-CH$_3$ | penta-F | | |
| 1.368 | 4-OEt | Cl | H | 2-CH$_3$ | penta-F | | |
| 1.369 | 4-OCF$_3$ | Cl | H | 2-CH$_3$ | penta-F | | |
| 1.370 | 4-CH$_3$ | Cl | H | 2-CH$_3$ | penta-F | | |
| 1.371 | 4-t-C$_4$H$_9$ | Cl | H | 2-CH$_3$ | penta-F | | |

TABLE 2

Compounds of the structure Ib where $R^3$, $R^4$ = halogen

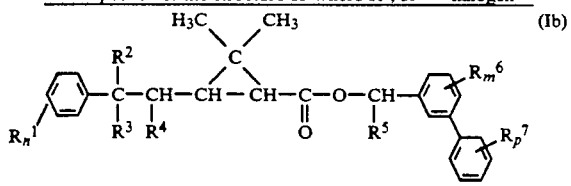
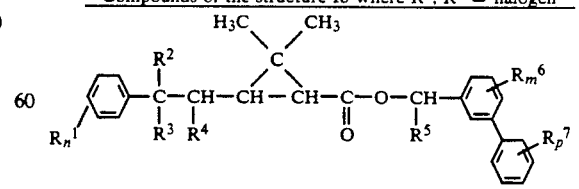

| Compound No. | $R_n^1$ | $R^2$ | $R^3$ | $R^4$ | $R^5$ | $R_m^6$ | $R_p^7$ |
|---|---|---|---|---|---|---|---|
| 2.1 | 4-CF$_3$ | Cl | Br | Br | H | 2-CH$_3$ | H |
| 2.2 | 4-CF$_3$ | Cl | Cl | Cl | H | 2-CH$_3$ | H |
| 2.3 | 4-CF$_3$ | Br | Br | Br | H | 2-CH$_3$ | H |
| 2.4 | 4-CF$_3$ | Br | Cl | Cl | H | 2-CH$_3$ | H |
| 2.5 | 4-Cl | Cl | Br | Br | H | 2-CH$_3$ | H |
| 2.6 | 4-Cl | Br | Br | Br | H | 2-CH$_3$ | H |
| 2.7 | 4-Cl | Cl | Cl | Cl | H | 2-CH$_3$ | H |
| 2.8 | 4-Cl | Br | Cl | Cl | H | 2-CH$_3$ | H |

TABLE 2-continued

Compounds of the structure Ib where $R^3$, $R^4$ = halogen $$\text{(Ib)}$$

| Compound No. | $R_n^1$ | $R^2$ | $R^3$ | $R^4$ | $R^5$ | $R_m^6$ | $R_p^7$ |
|---|---|---|---|---|---|---|---|
| 2.9 | 4-F | Cl | Br | Br | H | 2-CH$_3$ | H |
| 2.10 | 4-F | Br | Br | Br | H | 2-CH$_3$ | H |
| 2.11 | 4-F | Cl | Cl | Cl | H | 2-CH$_3$ | H |
| 2.12 | 4-F | Br | Cl | Cl | H | 2-CH$_3$ | H |
| 2.13 | 4-OCH$_3$ | Cl | Br | Br | H | 2-CH$_3$ | H |
| 2.14 | 4-OCH$_3$ | Br | Br | Br | H | 2-CH$_3$ | H |
| 2.15 | 4-OCH$_3$ | Cl | Cl | Cl | H | 2-CH$_3$ | H |
| 2.16 | 4-OCH$_3$ | Br | Cl | Cl | H | 2-CH$_3$ | H |
| 2.17 | 4-OC$_2$H$_5$ | Cl | Br | Br | H | 2-CH$_3$ | H |
| 2.18 | 4-OC$_2$H$_5$ | Br | Br | Br | H | 2-CH$_3$ | H |
| 2.19 | 4-OC$_2$H$_5$ | Cl | Br | Br | H | 2-CH$_3$ | H |
| 2.20 | 4-OC$_2$H$_5$ | Cl | Cl | Cl | H | 2-CH$_3$ | H |
| 2.21 | 4-OCF$_3$ | Cl | Br | Br | H | 2-CH$_3$ | H |
| 2.22 | 4-OCF$_3$ | Br | Br | Br | H | 2-CH$_3$ | H |
| 2.23 | 4-OCF$_3$ | Cl | Cl | Cl | H | 2-CH$_3$ | H |
| 2.24 | 4-OCF$_3$ | Br | Cl | Cl | H | 2-CH$_3$ | H |
| 2.25 | 3,4-O-CH$_2$-O | Cl | Br | Br | H | 2-CH$_3$ | H |
| 2.26 | 3,4-O-CH$_2$-O | Br | Br | Br | H | 2-CH$_3$ | H |
| 2.27 | 3,4-O-CH$_2$-O | Cl | Cl | Cl | H | 2-CH$_3$ | H |
| 2.28 | 3,4-O-CH$_2$-O | Br | Cl | Cl | H | 2-CH$_3$ | H |
| 2.29 | 3,4-O-CF$_2$-O | Cl | Br | Br | H | 2-CH$_3$ | H |
| 2.30 | 3,4-O-CF$_2$-O | Br | Br | Br | H | 2-CH$_3$ | H |
| 2.31 | 3,4-O-CF$_2$-O | Cl | Cl | Cl | H | 2-CH$_3$ | H |
| 2.32 | 3,4-O-CF$_2$-O | Br | Cl | Cl | H | 2-CH$_3$ | H |
| 2.33 | 4-CH$_3$ | Cl | Br | Br | H | 2-CH$_3$ | H |
| 2.34 | 4-CH$_3$ | Br | Br | Br | H | 2-CH$_3$ | H |
| 2.35 | 4-CH$_3$ | Cl | Cl | Cl | H | 2-CH$_3$ | H |
| 2.36 | 4-CH$_3$ | Br | Cl | Cl | H | 2-CH$_3$ | H |
| 2.37 | 4-t-C$_4$H$_9$ | Cl | Br | Br | H | 2-CH$_3$ | H |
| 2.38 | 4-t-C$_4$H$_9$ | Br | Br | Br | H | 2-CH$_3$ | H |
| 2.39 | 4-t-C$_4$H$_9$ | Cl | Cl | Cl | H | 2-CH$_3$ | H |
| 2.40 | 4-t-C$_4$H$_9$ | Br | Cl | Cl | H | 2-CH$_3$ | H |
| 2.41 | 4-CF$_3$, 2-Cl | Cl | Br | Br | H | 2-CH$_3$ | H |
| 2.42 | 4-CF$_3$, 2-Cl | Br | Br | Br | H | 2-CH$_3$ | H |
| 2.43 | 4-CF$_3$, 2-Cl | Cl | Cl | Cl | H | 2-CH$_3$ | H |
| 2.44 | 4-CF$_3$, 2-Cl | Br | Cl | Cl | H | 2-CH$_3$ | H |
| 2.45 | penta-F | Cl | Br | Br | H | 2-CH$_3$ | H |
| 2.46 | 4-CF$_3$ | Cl | Br | Br | H | 2-Cl | H |
| 2.47 | 4-CF$_3$ | Cl | Cl | Cl | H | 2-Cl | H |
| 2.48 | 4-CF$_3$ | Br | Br | Br | H | 2-Cl | H |
| 2.49 | 4-CF$_3$ | Br | Cl | Cl | H | 2-Cl | H |
| 2.50 | 4-Cl | Cl | Br | Br | H | 2-Cl | H |
| 2.51 | 4-Cl | Br | Br | Br | H | 2-Cl | H |
| 2.52 | 4-Cl | Cl | Cl | Cl | H | 2-Cl | H |
| 2.53 | 4-Cl | Br | Cl | Cl | H | 2-Cl | H |
| 2.54 | 4-F | Cl | Br | Br | H | 2-Cl | H |
| 2.55 | 4-F | Br | Br | Br | H | 2-Cl | H |
| 2.56 | 4-F | Cl | Cl | Cl | H | 2-Cl | H |
| 2.57 | 4-F | Br | Cl | Cl | H | 2-Cl | H |
| 2.58 | 4-OCH$_3$ | Cl | Br | Br | H | 2-Cl | H |
| 2.59 | 4-OCH$_3$ | Br | Br | Br | H | 2-Cl | H |
| 2.60 | 4-OCH$_3$ | Cl | Cl | Cl | H | 2-Cl | H |
| 2.61 | 4-OCH$_3$ | Br | Cl | Cl | H | 2-Cl | H |
| 2.62 | 4-OC$_2$H$_5$ | Cl | Br | Br | H | 2-Cl | H |
| 2.63 | 4-OC$_2$H$_5$ | Br | Br | Br | H | 2-Cl | H |
| 2.64 | 4-OC$_2$H$_5$ | Cl | Br | Br | H | 2-Cl | H |
| 2.65 | 4-OC$_2$H$_5$ | Cl | Cl | Cl | H | 2-Cl | H |
| 2.66 | 4-OCF$_3$ | Cl | Br | Br | H | 2-Cl | H |
| 2.67 | 4-OCF$_3$ | Br | Br | Br | H | 2-Cl | H |
| 2.68 | 4-OCF$_3$ | Cl | Cl | Cl | H | 2-Cl | H |
| 2.69 | 4-OCF$_3$ | Br | Cl | Cl | H | 2-Cl | H |
| 2.70 | 3,4-O-CH$_2$-O | Cl | Br | Br | H | 2-Cl | H |
| 2.71 | 3,4-O-CH$_2$-O | Br | Br | Br | H | 2-Cl | H |
| 2.72 | 3,4-O-CH$_2$-O | Cl | Cl | Cl | H | 2-Cl | H |
| 2.73 | 3,4-O-CH$_2$-O | Br | Cl | Cl | H | 2-Cl | H |
| 2.74 | 3,4-O-CF$_2$-O | Cl | Br | Br | H | 2-Cl | H |
| 2.75 | 3,4-O-CF$_2$-O | Br | Br | Br | H | 2-Cl | H |
| 2.76 | 3,4-O-CF$_2$-O | Cl | Cl | Cl | H | 2-Cl | H |

TABLE 2-continued

Compounds of the structure Ib where $R^3$, $R^4$ = halogen $$\text{R}_n^1\text{-C}_6\text{H}_4\text{-C}(R^2)(R^3)\text{-CH}(R^4)\text{-CH}[C(CH_3)_2]\text{-C}(=O)\text{-O-CH}(R^5)\text{-C}_6\text{H}_3(R_m^6)(R_p^7\text{-C}_6\text{H}_4)\quad (Ib)$$

| Compound No. | $R_n^1$ | $R^2$ | $R^3$ | $R^4$ | $R^5$ | $R_m^6$ | $R_p^7$ |
|---|---|---|---|---|---|---|---|
| 2.77 | 3,4-O-CF$_2$-O | Br | Cl | Cl | H | 2-Cl | H |
| 2.78 | 4-CH$_3$ | Cl | Br | Br | H | 2-Cl | H |
| 2.79 | 4-CH$_3$ | Br | Br | Br | H | 2-Cl | H |
| 2.80 | 4-CH$_3$ | Cl | Cl | Cl | H | 2-Cl | H |
| 2.81 | 4-CH$_3$ | Br | Cl | Cl | H | 2-Cl | H |
| 2.82 | 4-t-C$_4$H$_9$ | Cl | Br | Br | H | 2-Cl | H |
| 2.83 | 4-t-C$_4$H$_9$ | Br | Br | Br | H | 2-Cl | H |
| 2.84 | 4-t-C$_4$H$_9$ | Cl | Cl | Cl | H | 2-Cl | H |
| 2.85 | 4-t-C$_4$H$_9$ | Br | Cl | Cl | H | 2-Cl | H |
| 2.86 | 4-CF$_3$, 2-Cl | Cl | Br | Br | H | 2-Cl | H |
| 2.87 | 4-CF$_3$, 2-Cl | Br | Br | Br | H | 2-Cl | H |
| 2.88 | 4-CF$_3$, 2-Cl | Cl | Cl | Cl | H | 2-Cl | H |
| 2.89 | 4-CF$_3$, 2-Cl | Br | Cl | Cl | H | 2-Cl | H |
| 2.90 | penta-F | Cl | Br | Br | H | 2-Cl | H |
| 2.91 | 4-CF$_3$ | Cl | Br | Br | H | 2-F | H |
| 2.92 | 4-CF$_3$ | Cl | Cl | Cl | H | 2-F | H |
| 2.93 | 4-CF$_3$ | Br | Br | Br | H | 2-F | H |
| 2.94 | 4-CF$_3$ | Br | Cl | Cl | H | 2-F | H |
| 2.95 | 4-Cl | Cl | Br | Br | H | 2-F | H |
| 2.96 | 4-Cl | Br | Br | Br | H | 2-F | H |
| 2.97 | 4-Cl | Cl | Cl | Cl | H | 2-F | H |
| 2.98 | 4-Cl | Br | Cl | Cl | H | 2-F | H |
| 2.99 | 4-F | Cl | Br | Br | H | 2-F | H |
| 2.100 | 4-F | Br | Br | Br | H | 2-F | H |
| 2.101 | 4-F | Cl | Cl | Cl | H | 2-F | H |
| 2.102 | 4-F | Br | Cl | Cl | H | 2-F | H |
| 2.103 | 4-OCH$_3$ | Cl | Br | Br | H | 2-F | H |
| 2.104 | 4-OCH$_3$ | Br | Br | Br | H | 2-F | H |
| 2.105 | 4-OCH$_3$ | Cl | Cl | Cl | H | 2-F | H |
| 2.106 | 4-OCH$_3$ | Br | Cl | Cl | H | 2-F | H |
| 2.107 | 4-OC$_2$H$_5$ | Cl | Br | Br | H | 2-F | H |
| 2.108 | 4-OC$_2$H$_5$ | Br | Br | Br | H | 2-F | H |
| 2.109 | 4-OC$_2$H$_5$ | Cl | Cl | Cl | H | 2-F | H |
| 2.110 | 4-OC$_2$H$_5$ | Br | Cl | Cl | H | 2-F | H |
| 2.111 | 4-OCF$_3$ | Cl | Br | Br | H | 2-F | H |
| 2.112 | 4-OCF$_3$ | Br | Br | Br | H | 2-F | H |
| 2.113 | 4-OCF$_3$ | Cl | Cl | Cl | H | 2-F | H |
| 2.114 | 4-OCF$_3$ | Br | Cl | Cl | H | 2-F | H |
| 2.115 | 3,4-O-CH$_2$-O | Cl | Br | Br | H | 2-F | H |
| 2.116 | 3,4-O-CH$_2$-O | Br | Br | Br | H | 2-F | H |
| 2.117 | 3,4-O-CH$_2$-O | Cl | Cl | Cl | H | 2-F | H |
| 2.118 | 3,4-O-CH$_2$-O | Br | Cl | Cl | H | 2-F | H |
| 2.119 | 3,4-O-CF$_2$-O | Cl | Br | Br | H | 2-F | H |
| 2.120 | 3,4-O-CF$_2$-O | Br | Br | Br | H | 2-F | H |
| 2.121 | 3,4-O-CF$_2$-O | Cl | Cl | Cl | H | 2-F | H |
| 2.122 | 3,4-O-CF$_2$-O | Br | Cl | Cl | H | 2-F | H |
| 2.123 | 4-CH$_3$ | Cl | Br | Br | H | 2-F | H |
| 2.124 | 4-CH$_3$ | Br | Br | Br | H | 2-F | H |
| 2.125 | 4-CH$_3$ | Cl | Cl | Cl | H | 2-F | H |
| 2.126 | 4-CH$_3$ | Br | Cl | Cl | H | 2-F | H |
| 2.127 | 4-t-C$_4$H$_9$ | Cl | Br | Br | H | 2-F | H |
| 2.128 | 4-t-C$_4$H$_9$ | Br | Br | Br | H | 2-F | H |
| 2.129 | 4-t-C$_4$H$_9$ | Cl | Cl | Cl | H | 2-F | H |
| 2.130 | 4-t-C$_4$H$_9$ | Br | Cl | Cl | H | 2-F | H |
| 2.131 | 4-CF$_3$, 2-Cl | Cl | Br | Br | H | 2-F | H |
| 2.132 | 4-CF$_3$, 2-Cl | Br | Br | Br | H | 2-F | H |
| 2.133 | 4-CF$_3$, 2-Cl | Cl | Cl | Cl | H | 2-F | H |
| 2.134 | 4-CF$_3$, 2-Cl | Br | Cl | Cl | H | 2-F | H |
| 2.135 | penta-F | Cl | Br | Br | H | 2-F | H |
| 2.136 | 4-CF$_3$ | Cl | Br | Br | H | 2-CH$_3$, 4-F | H |
| 2.137 | 4-CF$_3$ | Cl | Cl | Cl | H | 2-CH$_3$, 4-F | H |
| 2.138 | 4-CF$_3$ | Br | Br | Br | H | 2-CH$_3$, 4-F | H |
| 2.139 | 4-CF$_3$ | Br | Cl | Cl | H | 2-CH$_3$, 4-F | H |
| 2.140 | 4-Cl | Cl | Br | Br | H | 2-CH$_3$, 4-F | H |
| 2.141 | 4-Cl | Br | Br | Br | H | 2-CH$_3$, 4-F | H |
| 2.142 | 4-Cl | Cl | Cl | Cl | H | 2-CH$_3$, 4-F | H |
| 2.143 | 4-Cl | Br | Cl | Cl | H | 2-CH$_3$, 4-F | H |
| 2.144 | 4-F | Cl | Br | Br | H | 2-CH$_3$, 4-F | H |
| 2.145 | 4-F | Br | Br | Br | H | 2-CH$_3$, 4-F | H |
| 2.146 | 4-F | Cl | Cl | Cl | H | 2-CH$_3$, 4-F | H |
| 2.147 | 4-F | Br | Cl | Cl | H | 2-CH$_3$, 4-F | H |
| 2.148 | 4-OCH$_3$ | Cl | Br | Br | H | 2-CH$_3$, 4-F | H |
| 2.149 | 4-OCH$_3$ | Br | Br | Br | H | 2-CH$_3$, 4-F | H |
| 2.150 | 4-OCH$_3$ | Cl | Cl | Cl | H | 2-CH$_3$, 4-F | H |
| 2.151 | 4-OCH$_3$ | Br | Cl | Cl | H | 2-CH$_3$, 4-F | H |
| 2.152 | 4-OC$_2$H$_5$ | Cl | Br | Br | H | 2-CH$_3$, 4-F | H |
| 2.153 | 4-OC$_2$H$_5$ | Br | Br | Br | H | 2-CH$_3$, 4-F | H |
| 2.154 | 4-OC$_2$H$_5$ | Cl | Cl | Cl | H | 2-CH$_3$, 4-F | H |
| 2.155 | 4-OC$_2$H$_5$ | Br | Cl | Cl | H | 2-CH$_3$, 4-F | H |
| 2.156 | 4-OCF$_3$ | Cl | Br | Br | H | 2-CH$_3$, 4-F | H |
| 2.157 | 4-OCF$_3$ | Br | Br | Br | H | 2-CH$_3$, 4-F | H |
| 2.158 | 4-OCF$_3$ | Cl | Cl | Cl | H | 2-CH$_3$, 4-F | H |
| 2.159 | 4-OCF$_3$ | Br | Cl | Cl | H | 2-CH$_3$, 4-F | H |
| 2.160 | 3,4-O-CH$_2$-O | Cl | Br | Br | H | 2-CH$_3$, 4-F | H |
| 2.161 | 3,4-O-CH$_2$-O | Br | Br | Br | H | 2-CH$_3$, 4-F | H |

TABLE 2-continued

Compounds of the structure Ib where $R^3$, $R^4$ = halogen (Ib)

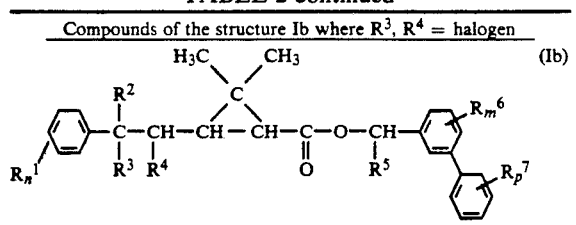

| Compound No. | $R_n^1$ | $R^2$ | $R^3$ | $R^4$ | $R^5$ | $R_m^6$ | $R_p^7$ |
|---|---|---|---|---|---|---|---|
| 2.162 | 3,4-OCH₂O | Cl | Cl | Cl | H | 2-CH₃, 4-F | H |
| 2.163 | 3,4-OCH₂O | Br | Cl | Cl | H | 2-CH₃, 4-F | H |
| 2.164 | 3,4-OCF₂O | Cl | Br | Br | H | 2-CH₃, 4-F | H |
| 2.165 | 3,4-OCF₂O | Br | Br | Br | H | 2-CH₃, 4-F | H |
| 2.166 | 3,4-OCF₂O | Cl | Cl | Cl | H | 2-CH₃, 4-F | H |
| 2.167 | 3,4-OCF₂O | Br | Cl | Cl | H | 2-CH₃, 4-F | H |
| 2.168 | 4-CH₃ | Cl | Br | Br | H | 2-CH₃, 4-F | H |
| 2.169 | 4-CH₃ | Br | Br | Br | H | 2-CH₃, 4-F | H |
| 2.170 | 4-CH₃ | Cl | Cl | Cl | H | 2-CH₃, 4-F | H |
| 2.171 | 4-CH₃ | Br | Cl | Cl | H | 2-CH₃, 4-F | H |
| 2.172 | 4-t-C₄H₉ | Cl | Br | Br | H | 2-CH₃, 4-F | H |
| 2.173 | 4-t-C₄H₉ | Br | Br | Br | H | 2-CH₃, 4-F | H |
| 2.174 | 4-t-C₄H₉ | Cl | Cl | Cl | H | 2-CH₃, 4-F | H |
| 2.175 | 4-t-C₄H₉ | Br | Cl | Cl | H | 2-CH₃, 4-F | H |
| 2.176 | 4-CF₃, 2-Cl | Cl | Br | Br | H | 2-CH₃, 4-F | H |
| 2.177 | 4-CF₃, 2-Cl | Br | Br | Br | H | 2-CH₃, 4-F | H |
| 2.178 | 4-CF₃, 2-Cl | Cl | Cl | Cl | H | 2-CH₃, 4-F | H |
| 2.179 | 4-CF₃, 2-Cl | Br | Cl | Cl | H | 2-CH₃, 4-F | H |
| 2.180 | penta-F | Cl | Br | Br | H | 2-CH₃, 4-F | H |
| 2.181 | 4-CF₃ | Cl | Br | Br | H | 2,4-Cl₂ | H |
| 2.182 | 4-CF₃ | Cl | Cl | Cl | H | 2,4-Cl₂ | H |
| 2.183 | 4-CF₃ | Br | Br | Br | H | 2,4-Cl₂ | H |
| 2.184 | 4-CF₃ | Br | Cl | Cl | H | 2,4-Cl₂ | H |
| 2.185 | 4-Cl | Cl | Br | Br | H | 2,4-Cl₂ | H |
| 2.186 | 4-Cl | Br | Br | Br | H | 2,4-Cl₂ | H |
| 2.187 | 4-Cl | Cl | Cl | Cl | H | 2,4-Cl₂ | H |
| 2.188 | 4-Cl | Br | Cl | Cl | H | 2,4-Cl₂ | H |
| 2.189 | 4-F | Cl | Br | Br | H | 2,4-Cl₂ | H |
| 2.190 | 4-F | Br | Br | Br | H | 2,4-Cl₂ | H |
| 2.191 | 4-F | Cl | Cl | Cl | H | 2,4-Cl₂ | H |
| 2.192 | 4-F | Br | Cl | Cl | H | 2,4-Cl₂ | H |
| 2.193 | 4-OCH₃ | Cl | Br | Br | H | 2,4-Cl₂ | H |
| 2.194 | 4-OCH₃ | Br | Br | Br | H | 2,4-Cl₂ | H |
| 2.195 | 4-OCH₃ | Cl | Cl | Cl | H | 2,4-Cl₂ | H |
| 2.196 | 4-OCH₃ | Br | Cl | Cl | H | 2,4-Cl₂ | H |
| 2.197 | 4-OC₂H₅ | Cl | Br | Br | H | 2,4-Cl₂ | H |
| 2.198 | 4-OC₂H₅ | Br | Br | Br | H | 2,4-Cl₂ | H |
| 2.199 | 4-OC₂H₅ | Cl | Br | Br | H | 2,4-Cl₂ | H |
| 2.200 | 4-OC₂H₅ | Br | Cl | Cl | H | 2,4-Cl₂ | H |
| 2.201 | 4-OCF₃ | Cl | Br | Br | H | 2,4-Cl₂ | H |
| 2.202 | 4-OCF₃ | Br | Br | Br | H | 2,4-Cl₂ | H |
| 2.203 | 4-OCF₃ | Cl | Cl | Cl | H | 2,4-Cl₂ | H |
| 2.204 | 4-OCF₃ | Br | Cl | Cl | H | 2,4-Cl₂ | H |
| 2.205 | 3,4-OCH₂O | Cl | Br | Br | H | 2,4-Cl₂ | H |
| 2.206 | 3,4-OCH₂O | Br | Br | Br | H | 2,4-Cl₂ | H |
| 2.207 | 3,4-OCH₂O | Cl | Cl | Cl | H | 2,4-Cl₂ | H |
| 2.208 | 3,4-OCH₂O | Br | Cl | Cl | H | 2,4-Cl₂ | H |
| 2.209 | 3,4-OCF₂O | Cl | Br | Br | H | 2,4-Cl₂ | H |
| 2.210 | 3,4-OCF₂O | Br | Br | Br | H | 2,4-Cl₂ | H |
| 2.211 | 3,4-OCF₂O | Cl | Cl | Cl | H | 2,4-Cl₂ | H |
| 2.212 | 3,4-OCF₂O | Br | Cl | Cl | H | 2,4-Cl₂ | H |
| 2.213 | 4-CH₃ | Cl | Br | Br | H | 2,4-Cl₂ | H |
| 2.214 | 4-CH₃ | Br | Br | Br | H | 2,4-Cl₂ | H |
| 2.215 | 4-CH₃ | Cl | Cl | Cl | H | 2,4-Cl₂ | H |
| 2.216 | 4-CH₃ | Br | Cl | Cl | H | 2,4-Cl₂ | H |
| 2.217 | 4-t-C₄H₉ | Cl | Br | Br | H | 2,4-Cl₂ | H |
| 2.218 | 4-t-C₄H₉ | Br | Br | Br | H | 2,4-Cl₂ | H |
| 2.219 | 4-t-C₄H₉ | Cl | Cl | Cl | H | 2,4-Cl₂ | H |
| 2.220 | 4-t-C₄H₉ | Br | Cl | Cl | H | 2,4-Cl₂ | H |
| 2.221 | 4-CF₃, 2-Cl | Cl | Br | Br | H | 2,4-Cl₂ | H |
| 2.222 | 4-CF₃, 2-Cl | Br | Br | Br | H | 2,4-Cl₂ | H |
| 2.223 | 4-CF₃, 2-Cl | Cl | Cl | Cl | H | 2,4-Cl₂ | H |
| 2.224 | 4-CF₃, 2-Cl | Br | Cl | Cl | H | 2,4-Cl₂ | H |
| 2.225 | penta-F | Cl | Br | Br | H | 2,4-Cl₂ | H |
| 2.226 | 4-CF₃ | Cl | Br | Br | H | tetra-F | H |
| 2.227 | 4-CF₃ | Cl | Cl | Cl | H | tetra-F | H |
| 2.228 | 4-CF₃ | Br | Br | Br | H | tetra-F | H |
| 2.229 | 4-CF₃ | Br | Cl | Cl | H | tetra-F | H |
| 2.230 | 4-Cl | Cl | Br | Br | H | tetra-F | H |
| 2.231 | 4-Cl | Br | Br | Br | H | tetra-F | H |
| 2.232 | 4-Cl | Cl | Cl | Cl | H | tetra-F | H |
| 2.233 | 4-Cl | Br | Cl | Cl | H | tetra-F | H |
| 2.234 | 4-F | Cl | Br | Br | H | tetra-F | H |
| 2.235 | 4-F | Br | Br | Br | H | tetra-F | H |
| 2.236 | 4-F | Cl | Cl | Cl | H | tetra-F | H |
| 2.237 | 4-F | Br | Cl | Cl | H | tetra-F | H |

TABLE 2-continued

Compounds of the structure Ib where $R^3$, $R^4$ = halogen

(Ib)

| Compound No. | $R_n^1$ | $R^2$ | $R^3$ | $R^4$ | $R^5$ | $R_m^6$ | $R_p^7$ |
|---|---|---|---|---|---|---|---|
| 2.238 | 4-OCH₃ | Cl | Br | Br | H | tetra-F | H |
| 2.239 | 4-OCH₃ | Br | Br | Br | H | tetra-F | H |
| 2.240 | 4-OCH₃ | Cl | Cl | Cl | H | tetra-F | H |
| 2.241 | 4-OCH₃ | Br | Cl | Cl | H | tetra-F | H |
| 2.242 | 4-OC₂H₅ | Cl | Br | Br | H | tetra-F | H |
| 2.243 | 4-OC₂H₅ | Br | Br | Br | H | tetra-F | H |
| 2.244 | 4-OC₂H₅ | Cl | Br | Br | H | tetra-F | H |
| 2.245 | 4-OC₂H₅ | Cl | Cl | Cl | H | tetra-F | H |
| 2.246 | 4-OCF₃ | Cl | Br | Br | H | tetra-F | H |
| 2.247 | 4-OCF₃ | Br | Br | Br | H | tetra-F | H |
| 2.248 | 4-OCF₃ | Cl | Cl | Cl | H | tetra-F | H |
| 2.249 | 4-OCF₃ | Br | Cl | Cl | H | tetra-F | H |
| 2.250 | 3,4-O-CH₂-O | Cl | Br | Br | H | tetra-F | H |
| 2.251 | 3,4-O-CH₂-O | Br | Br | Br | H | tetra-F | H |
| 2.252 | 3,4-O-CH₂-O | Cl | Cl | Cl | H | tetra-F | H |
| 2.253 | 3,4-O-CH₂-O | Br | Cl | Cl | H | tetra-F | H |
| 2.254 | 3,4-O-CF₂-O | Cl | Br | Br | H | tetra-F | H |
| 2.255 | 3,4-O-CF₂-O | Br | Br | Br | H | tetra-F | H |
| 2.256 | 3,4-O-CF₂-O | Cl | Cl | Cl | H | tetra-F | H |
| 2.257 | 3,4-O-CF₂-O | Br | Cl | Cl | H | tetra-F | H |
| 2.258 | 4-CH₃ | Cl | Br | Br | H | tetra-F | H |
| 2.259 | 4-CH₃ | Br | Br | Br | H | tetra-F | H |
| 2.260 | 4-CH₃ | Cl | Cl | Cl | H | tetra-F | H |
| 2.261 | 4-CH₃ | Br | Cl | Cl | H | tetra-F | H |
| 2.262 | 4-t-C₄H₉ | Cl | Br | Br | H | tetra-F | H |
| 2.263 | 4-t-C₄H₉ | Br | Br | Br | H | tetra-F | H |
| 2.264 | 4-t-C₄H₉ | Cl | Cl | Cl | H | tetra-F | H |
| 2.265 | 4-t-C₄H₉ | Br | Cl | Cl | H | tetra-F | H |
| 2.266 | 4-CF₃, 2-Cl | Cl | Br | Br | H | tetra-F | H |
| 2.267 | 4-CF₃, 2-Cl | Br | Br | Br | H | tetra-F | H |
| 2.268 | 4-CF₃, 2-Cl | Cl | Cl | Cl | H | tetra-F | H |
| 2.269 | 4-CF₃, 2-Cl | Br | Cl | Cl | H | tetra-F | H |
| 2.270 | penta-F | Cl | Br | Br | H | tetra-F | H |
| 2.271 | 4-CF₃ | Cl | Br | Br | H | 2-CH₃ | 4-F |
| 2.272 | 4-CF₃ | Cl | Cl | Cl | H | 2-CH₃ | 4-F |
| 2.273 | 4-CF₃ | Br | Br | Br | H | 2-CH₃ | 4-F |
| 2.274 | 4-CF₃ | Br | Cl | Cl | H | 2-CH₃ | 4-F |
| 2.275 | 4-Cl | Cl | Br | Br | H | 2-CH₃ | 4-F |
| 2.276 | 4-Cl | Br | Br | Br | H | 2-CH₃ | 4-F |
| 2.277 | 4-Cl | Cl | Cl | Cl | H | 2-CH₃ | 4-F |
| 2.278 | 4-Cl | Br | Cl | Cl | H | 2-CH₃ | 4-F |
| 2.279 | 4-F | Cl | Br | Br | H | 2-CH₃ | 4-F |
| 2.280 | 4-F | Br | Br | Br | H | 2-CH₃ | 4-F |
| 2.281 | 4-F | Cl | Cl | Cl | H | 2-CH₃ | 4-F |
| 2.282 | 4-F | Br | Cl | Cl | H | 2-CH₃ | 4-F |
| 2.283 | 4-OCH₃ | Cl | Br | Br | H | 2-CH₃ | 4-F |
| 2.284 | 4-OCH₃ | Br | Br | Br | H | 2-CH₃ | 4-F |
| 2.285 | 4-OCH₃ | Cl | Cl | Cl | H | 2-CH₃ | 4-F |
| 2.286 | 4-OCH₃ | Br | Cl | Cl | H | 2-CH₃ | 4-F |
| 2.287 | 4-OC₂H₅ | Cl | Br | Br | H | 2-CH₃ | 4-F |
| 2.288 | 4-OC₂H₅ | Br | Br | Br | H | 2-CH₃ | 4-F |
| 2.289 | 4-OC₂H₅ | Cl | Br | Br | H | 2-CH₃ | 4-F |
| 2.290 | 4-OC₂H₅ | Cl | Cl | Cl | H | 2-CH₃ | 4-F |
| 2.291 | 4-OCF₃ | Cl | Br | Br | H | 2-CH₃ | 4-F |
| 2.292 | 4-OCF₃ | Br | Br | Br | H | 2-CH₃ | 4-F |
| 2.293 | 4-OCF₃ | Cl | Cl | Cl | H | 2-CH₃ | 4-F |
| 2.294 | 4-OCF₃ | Br | Cl | Cl | H | 2-CH₃ | 4-F |
| 2.295 | 3,4-O-CH₂-O | Cl | Br | Br | H | 2-CH₃ | 4-F |
| 2.296 | 3,4-O-CH₂-O | Br | Br | Br | H | 2-CH₃ | 4-F |
| 2.297 | 3,4-O-CH₂-O | Cl | Cl | Cl | H | 2-CH₃ | 4-F |
| 2.298 | 3,4-O-CH₂-O | Br | Cl | Cl | H | 2-CH₃ | 4-F |
| 2.299 | 3,4-O-CF₂-O | Cl | Br | Br | H | 2-CH₃ | 4-F |
| 2.300 | 3,4-O-CF₂-O | Br | Br | Br | H | 2-CH₃ | 4-F |
| 2.301 | 3,4-O-CF₂-O | Cl | Cl | Cl | H | 2-CH₃ | 4-F |
| 2.302 | 3,4-O-CF₂-O | Br | Cl | Cl | H | 2-CH₃ | 4-F |
| 2.303 | 4-CH₃ | Cl | Br | Br | H | 2-CH₃ | 4-F |

TABLE 2-continued

Compounds of the structure Ib where $R^3$, $R^4$ = halogen

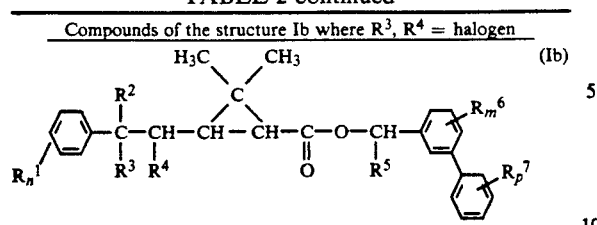

(Ib)

| Compound No. | $R_n^1$ | $R^2$ | $R^3$ | $R^4$ | $R^5$ | $R_m^6$ | $R_p^7$ |
|---|---|---|---|---|---|---|---|
| 2.304 | 4-CH₃ | Br | Br | Br | H | 2-CH₃ | 4-F |
| 2.305 | 4-CH₃ | Cl | Cl | Cl | H | 2-CH₃ | 4-F |
| 2.306 | 4-CH₃ | Br | Cl | Cl | H | 2-CH₃ | 4-F |
| 2.307 | 4-t-C₄H₉ | Cl | Br | Br | H | 2-CH₃ | 4-F |
| 2.308 | 4-t-C₄H₉ | Br | Br | Br | H | 2-CH₃ | 4-F |
| 2.309 | 4-t-C₄H₉ | Cl | Cl | Cl | H | 2-CH₃ | 4-F |
| 2.310 | 4-t-C₄H₉ | Br | Cl | Cl | H | 2-CH₃ | 4-F |
| 2.311 | 4-CF₃, 2-Cl | Cl | Br | Br | H | 2-CH₃ | 4-F |
| 2.312 | 4-CF₃, 2-Cl | Br | Br | Br | H | 2-CH₃ | 4-F |
| 2.313 | 4-CF₃, 2-Cl | Cl | Cl | Cl | H | 2-CH₃ | 4-F |
| 2.314 | 4-CF₃, 2-Cl | Br | Cl | Cl | H | 2-CH₃ | 4-F |
| 2.315 | penta-F | Cl | Br | Br | H | 2-CH₃ | 4-F |
| 2.316 | 4-CF₃ | Cl | Br | Br | H | 2-CH₃ | 4-Cl |
| 2.317 | 4-CF₃ | Cl | Cl | Cl | H | 2-CH₃ | 4-Cl |
| 2.318 | 4-CF₃ | Br | Br | Br | H | 2-CH₃ | 4-Cl |
| 2.319 | 4-CF₃ | Br | Cl | Cl | H | 2-CH₃ | 4-Cl |
| 2.320 | 4-Cl | Cl | Br | Br | H | 2-CH₃ | 4-Cl |
| 2.321 | 4-Cl | Br | Br | Br | H | 2-CH₃ | 4-Cl |
| 2.322 | 4-Cl | Cl | Cl | Cl | H | 2-CH₃ | 4-Cl |
| 2.323 | 4-Cl | Br | Cl | Cl | H | 2-CH₃ | 4-Cl |
| 2.324 | 4-F | Cl | Br | Br | H | 2-CH₃ | 4-Cl |
| 2.325 | 4-F | Br | Br | Br | H | 2-CH₃ | 4-Cl |
| 2.326 | 4-F | Cl | Cl | Cl | H | 2-CH₃ | 4-Cl |
| 2.327 | 4-F | Br | Cl | Cl | H | 2-CH₃ | 4-Cl |
| 2.328 | 4-OCH₃ | Cl | Br | Br | H | 2-CH₃ | 4-Cl |
| 2.329 | 4-OCH₃ | Br | Br | Br | H | 2-CH₃ | 4-Cl |
| 3.330 | 4-OCH₃ | Cl | Cl | Cl | H | 2-CH₃ | 4-Cl |
| 3.331 | 4-OCH₃ | Br | Cl | Cl | H | 2-CH₃ | 4-Cl |
| 3.332 | 4-OC₂H₅ | Cl | Br | Br | H | 2-CH₃ | 4-Cl |
| 2.333 | 4-OC₂H₅ | Br | Br | Br | H | 2-CH₃ | 4-Cl |
| 2.334 | 4-OC₂H₅ | Cl | Cl | Cl | H | 2-CH₃ | 4-Cl |
| 2.335 | 4-OC₂H₅ | Br | Cl | Cl | H | 2-CH₃ | 4-Cl |
| 2.336 | 4-OCF₃ | Cl | Br | Br | H | 2-CH₃ | 4-Cl |
| 2.337 | 4-OCF₃ | Br | Br | Br | H | 2-CH₃ | 4-Cl |
| 2.338 | 4-OCF₃ | Cl | Cl | Cl | H | 2-CH₃ | 4-Cl |
| 2.339 | 4-OCF₃ | Br | Cl | Cl | H | 2-CH₃ | 4-Cl |
| 2.340 | 3,4-OCH₂O | Cl | Br | Br | H | 2-CH₃ | 4-Cl |
| 2.341 | 3,4-OCH₂O | Br | Br | Br | H | 2-CH₃ | 4-Cl |
| 2.342 | 3,4-OCH₂O | Cl | Cl | Cl | H | 2-CH₃ | 4-Cl |
| 2.343 | 3,4-OCH₂O | Br | Cl | Cl | H | 2-CH₃ | 4-Cl |
| 2.344 | 3,4-OCF₂O | Cl | Br | Br | H | 2-CH₃ | 4-Cl |
| 2.345 | 3,4-OCF₂O | Br | Br | Br | H | 2-CH₃ | 4-Cl |
| 2.346 | 3,4-OCF₂O | Cl | Cl | Cl | H | 2-CH₃ | 4-Cl |
| 2.347 | 3,4-OCF₂O | Br | Cl | Cl | H | 2-CH₃ | 4-Cl |
| 2.348 | 4-CH₃ | Cl | Br | Br | H | 2-CH₃ | 4-Cl |
| 2.349 | 4-CH₃ | Br | Br | Br | H | 2-CH₃ | 4-Cl |
| 2.350 | 4-CH₃ | Cl | Cl | Cl | H | 2-CH₃ | 4-Cl |
| 2.351 | 4-CH₃ | Br | Cl | Cl | H | 2-CH₃ | 4-Cl |
| 2.352 | 4-t-C₄H₉ | Cl | Br | Br | H | 2-CH₃ | 4-Cl |
| 2.353 | 4-t-C₄H₉ | Br | Br | Br | H | 2-CH₃ | 4-Cl |
| 2.354 | 4-t-C₄H₉ | Cl | Cl | Cl | H | 2-CH₃ | 4-Cl |
| 2.355 | 4-t-C₄H₉ | Br | Cl | Cl | H | 2-CH₃ | 4-Cl |
| 2.356 | 4-CF₃, 2-Cl | Cl | Br | Br | H | 2-CH₃ | 4-Cl |
| 2.357 | 4-CF₃, 2-Cl | Br | Br | Br | H | 2-CH₃ | 4-Cl |
| 2.358 | 4-CF₃, 2-Cl | Cl | Cl | Cl | H | 2-CH₃ | 4-Cl |
| 2.359 | 4-CF₃, 2-Cl | Br | Cl | Cl | H | 2-CH₃ | 4-Cl |
| 2.360 | penta-F | Cl | Br | Br | H | 2-CH₃ | 4-Cl |
| 2.361 | 4-CF₃ | Cl | Br | Br | H | 2-CH₃ | penta F |
| 2.362 | 4-CF₃ | Cl | Cl | Cl | H | 2-CH₃ | penta F |
| 2.363 | 4-CF₃ | Br | Br | Br | H | 2-CH₃ | penta F |
| 2.364 | 4-CF₃ | Br | Cl | Cl | H | 2-CH₃ | penta F |
| 2.365 | 4-Cl | Cl | Br | Br | H | 2-CH₃ | penta F |
| 2.366 | 4-Cl | Br | Br | Br | H | 2-CH₃ | penta F |
| 2.367 | 4-Cl | Cl | Cl | Cl | H | 2-CH₃ | penta F |
| 2.368 | 4-Cl | Br | Cl | Cl | H | 2-CH₃ | penta F |
| 2.369 | 4-F | Cl | Br | Br | H | 2-CH₃ | penta F |
| 2.370 | 4-F | Br | Br | Br | H | 2-CH₃ | penta F |
| 2.371 | 4-F | Cl | Cl | Cl | H | 2-CH₃ | penta F |
| 2.372 | 4-F | Br | Cl | Cl | H | 2-CH₃ | penta F |
| 2.373 | 4-OCH₃ | Cl | Br | Br | H | 2-CH₃ | penta F |
| 2.374 | 4-OCH₃ | Br | Br | Br | H | 2-CH₃ | penta F |
| 2.375 | 4-OCH₃ | Cl | Cl | Cl | H | 2-CH₃ | penta F |
| 2.376 | 4-OCH₃ | Br | Cl | Cl | H | 2-CH₃ | penta F |
| 2.377 | 4-OC₂H₅ | Cl | Br | Br | H | 2-CH₃ | penta F |
| 2.378 | 4-OC₂H₅ | Br | Br | Br | H | 2-CH₃ | penta F |
| 2.379 | 4-OC₂H₅ | Cl | Cl | Cl | H | 2-CH₃ | penta F |
| 2.380 | 4-OC₂H₅ | Br | Cl | Cl | H | 2-CH₃ | penta F |
| 2.381 | 4-OCF₃ | Cl | Br | Br | H | 2-CH₃ | penta F |
| 2.382 | 4-OCF₃ | Br | Br | Br | H | 2-CH₃ | penta F |
| 2.383 | 4-OCF₃ | Cl | Cl | Cl | H | 2-CH₃ | penta F |
| 2.384 | 4-OCF₃ | Br | Cl | Cl | H | 2-CH₃ | penta F |
| 2.385 | 3,4-OCH₂O | Cl | Br | Br | H | 2-CH₃ | penta F |
| 2.386 | 3,4-OCH₂O | Br | Br | Br | H | 2-CH₃ | penta F |
| 2.387 | 3,4-OCH₂O | Cl | Cl | Cl | H | 2-CH₃ | penta F |
| 2.388 | 3,4-OCH₂O | Br | Cl | Cl | H | 2-CH₃ | penta F |

TABLE 2-continued

Compounds of the structure Ib where $R^3$, $R^4$ = halogen $$\underset{R_n^1}{\bigcirc}-\underset{R^3}{\overset{R^2}{\underset{|}{C}}}-CH-\underset{}{\overset{H_3C\ CH_3}{\underset{|}{C}}}-\underset{}{\overset{}{\underset{R^4}{C}H}}-\underset{O}{\overset{}{C}}-O-\underset{R^5}{\overset{}{C}H}-\underset{}{\bigcirc}\underset{R_p^7}{\overset{R_m^6}{}}$$ (Ib)

| Compound No. | $R_n^1$ | $R^2$ | $R^3$ | $R^4$ | $R^5$ | $R_m^6$ | $R_p^7$ |
|---|---|---|---|---|---|---|---|
| 2.389 | 3,4- O\CF2/O | | Cl | Br | Br | H | 2-CH₃ | penta F |
| 2.390 | 3,4- O\CF2/O | | Br | Br | Br | H | 2-CH₃ | penta F |
| 2.391 | 3,4- O\CF2/O | | Cl | Cl | Cl | H | 2-CH₃ | penta F |
| 2.392 | 3,4- O\CF2/O | | Br | Cl | Cl | H | 2-CH₃ | penta F |
| 2.393 | 4-CH₃ | | Cl | Br | Br | H | 2-CH₃ | penta F |
| 2.394 | 4-CH₃ | | Br | Br | Br | H | 2-CH₃ | penta F |
| 2.395 | 4-CH₃ | | Cl | Cl | Cl | H | 2-CH₃ | penta F |
| 2.396 | 4-CH₃ | | Br | Cl | Cl | H | 2-CH₃ | penta F |
| 2.397 | 4-t-C₄H₉ | | Cl | Br | Br | H | 2-CH₃ | penta F |
| 2.398 | 4-t-C₄H₉ | | Br | Br | Br | H | 2-CH₃ | penta F |
| 2.399 | 4-t-C₄H₉ | | Cl | Cl | Cl | H | 2-CH₃ | penta F |
| 2.400 | 4-t-C₄H₉ | | Cl | Cl | Cl | H | 2-CH₃ | penta F |
| 2.401 | 4-CF₃, 2-Cl | | Cl | Br | Br | H | 2-CH₃ | penta F |
| 2.402 | 4-CF₃, 2-Cl | | Br | Br | Br | H | 2-CH₃ | penta F |
| 2.403 | 4-CF₃, 2-Cl | | Cl | Cl | Cl | H | 2-CH₃ | penta F |
| 2.404 | 4-CF₃, 2-Cl | | Br | Cl | Cl | H | 2-CH₃ | penta F |
| 2.405 | penta-F | | Cl | Br | Br | H | 2-CH₃ | penta F |
| 2.406 | 4-CF₃ | | Cl | Br | Br | H | 2-CH₃ | 3,4-F₂ |
| 2.407 | 4-CF₃ | | Cl | Cl | Cl | H | 2-CH₃ | 3,4-F₂ |
| 2.408 | 4-CF₃ | | Br | Br | Br | H | 2-CH₃ | 3,4-F₂ |
| 2.409 | 4-CF₃ | | Br | Cl | Cl | H | 2-CH₃ | 3,4-F₂ |
| 2.410 | 4-Cl | | Cl | Br | Br | H | 2-CH₃ | 3,4-F₂ |
| 2.411 | 4-Cl | | Br | Br | Br | H | 2-CH₃ | 3,4-F₂ |
| 2.412 | 4-Cl | | Cl | Cl | Cl | H | 2-CH₃ | 3,4-F₂ |
| 2.413 | 4-Cl | | Br | Cl | Cl | H | 2-CH₃ | 3,4-F₂ |
| 2.414 | 4-F | | Cl | Br | Br | H | 2-CH₃ | 3,4-F₂ |
| 2.415 | 4-F | | Br | Br | Br | H | 2-CH₃ | 3,4-F₂ |
| 2.416 | 4-F | | Cl | Cl | Cl | H | 2-CH₃ | 3,4-F₂ |
| 2.417 | 4-F | | Br | Cl | Cl | H | 2-CH₃ | 3,4-F₂ |
| 2.418 | 4-OCH₃ | | Cl | Br | Br | H | 2-CH₃ | 3,4-F₂ |
| 2.419 | 4-OCH₃ | | Br | Br | Br | H | 2-CH₃ | 3,4-F₂ |
| 2.420 | 4-OCH₃ | | Cl | Cl | Cl | H | 2-CH₃ | 3,4-F₂ |
| 2.421 | 4-OCH₃ | | Br | Cl | Cl | H | 2-CH₃ | 3,4-F₂ |
| 2.422 | 4-OC₂H₅ | | Cl | Br | Br | H | 2-CH₃ | 3,4-F₂ |
| 2.423 | 4-OC₂H₅ | | Br | Br | Br | H | 2-CH₃ | 3,4-F₂ |
| 2.424 | 4-OC₂H₅ | | Cl | Cl | Cl | H | 2-CH₃ | 3,4-F₂ |
| 2.425 | 4-OC₂H₅ | | Cl | Cl | Cl | H | 2-CH₃ | 3,4-F₂ |
| 2.426 | 4-OCF₃ | | Cl | Br | Br | H | 2-CH₃ | 3,4-F₂ |
| 2.427 | 4-OCF₃ | | Br | Br | Br | H | 2-CH₃ | 3,4-F₂ |
| 2.428 | 4-OCF₃ | | Cl | Cl | Cl | H | 2-CH₃ | 3,4-F₂ |
| 2.429 | 4-OCF₃ | | Br | Cl | Cl | H | 2-CH₃ | 3,4-F₂ |
| 2.430 | 3,4- O\CH2/O | | Cl | Br | Br | H | 2-CH₃ | 3,4-F₂ |
| 2.431 | 3,4- O\CH2/O | | Br | Br | Br | H | 2-CH₃ | 3,4-F₂ |
| 2.432 | 3,4- O\CH2/O | | Cl | Cl | Cl | H | 2-CH₃ | 3,4-F₂ |
| 2.433 | 3,4- O\CH2/O | | Br | Cl | Cl | H | 2-CH₃ | 3,4-F₂ |
| 2.434 | 3,4- O\CF2/O | | Cl | Br | Br | H | 2-CH₃ | 3,4-F₂ |
| 2.435 | 3,4- O\CF2/O | | Br | Br | Br | H | 2-CH₃ | 3,4-F₂ |
| 2.436 | 3,4- O\CF2/O | | Cl | Cl | Cl | H | 2-CH₃ | 3,4-F₂ |
| 2.437 | 3,4- O\CF2/O | | Br | Cl | Cl | H | 2-CH₃ | 3,4-F₂ |
| 2.438 | 4-CH₃ | | Cl | Br | Br | H | 2-CH₃ | 3,4-F₂ |
| 2.439 | 4-CH₃ | | Br | Br | Br | H | 2-CH₃ | 3,4-F₂ |
| 2.440 | 4-CH₃ | | Cl | Cl | Cl | H | 2-CH₃ | 3,4-F₂ |
| 2.441 | 4-CH₃ | | Br | Cl | Cl | H | 2-CH₃ | 3,4-F₂ |
| 2.442 | 4-t-C₄H₉ | | Cl | Br | Br | H | 2-CH₃ | 3,4-F₂ |
| 2.443 | 4-t-C₄H₉ | | Br | Br | Br | H | 2-CH₃ | 3,4-F₂ |
| 2.444 | 4-t-C₄H₉ | | Cl | Cl | Cl | H | 2-CH₃ | 3,4-F₂ |
| 2.445 | 4-t-C₄H₉ | | Br | Cl | Cl | H | 2-CH₃ | 3,4-F₂ |
| 2.446 | 4-CF₃, 2-Cl | | Cl | Br | Br | H | 2-CH₃ | 3,4-F₂ |
| 2.447 | 4-CF₃, 2-Cl | | Br | Br | Br | H | 2-CH₃ | 3,4-F₂ |
| 2.448 | 4-CF₃, 2-Cl | | Cl | Cl | Cl | H | 2-CH₃ | 3,4-F₂ |
| 2.449 | 4-CF₃, 2-Cl | | Br | Cl | Cl | H | 2-CH₃ | 3,4-F₂ |
| 2.450 | penta-F | | Cl | Br | Br | H | 2-CH₃ | 3,4-F₂ |

USE EXAMPLES

In the following examples, Compound No. 1.1 was compared with prior art Compounds I and II.

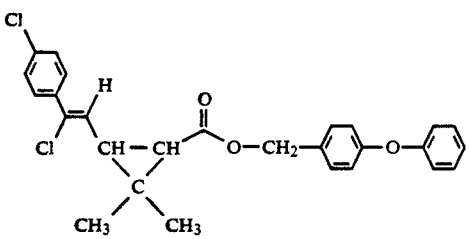

I

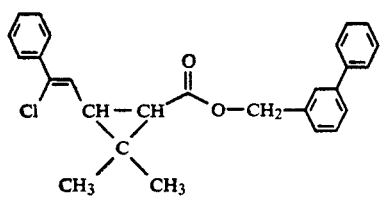

II

The purity of the substances was >95%. The concentrations at which the investigated compounds exhibit 100% kill are the minimum concentrations. At least two experiments were carried out for each concentration and an average was formed.

The active ingredient was used either as a 0.1% acetonic solution or as a 10% emulsions concentrate obtained by emulsifying the active ingredient in a mixture containing 70 wt % of cyclohexanone, 20 wt % of Nekanil® LN (=Lutensol AP6, a spreader-sticker with an emulsifying and dispersing action based on ethoxylated alkylphenols) and 10 wt % of Emulphor® EL (an emulsifier based on ethoxylated fatty alcohols). The concentrations given in the examples were obtained by diluting the formulated active ingredient with water.

Contact Action on Oriental Cockroaches (*Blatta orientalis*)

The bottoms of 1-liter jars were treated with acetonic solutions of the active ingredients. After the solvent had evaporated, 5 adult cockroaches were placed in each jar. The kill rate was determined after 48 hours.

In this experiment, compound no. 1.1 had an activity ten times greater than that of comparative substance I. Comparative substance II was ineffective at a concentration of 1 mg.

Contact Action on *Sitophilus granaria* (Granary Weevil)

The bottoms of glass Petri dishes 10 cm in diameter (the rims of which had been treated with FLUON) were treated with 1 cm³ of acetonic solutions of the active ingredients. After the acetone had evaporated, about 50 weevils were introduced into each dish.

After 4 hours, the weevils were transferred to cardboard dishes 40 mm in diameter and 10 mm high, which were then placed in the Petri dishes. The action was determined after 24 hours in percentage kill.

Weevils unable to leave the cardboard dishes were considered to be dead or heavily damaged.

In this experiment, compound 1.1 was superior to comparative substance I, and comparative substance II was ineffective at a concentration 10 times higher than the inventive compound.

Contact Action on *Aedes aegypti* (Yellow-fever Mosquito)

At 25° C., 200 ml of tapwater containing the active ingredients was filled into 250 ml plastic beakers; 20 to 30 mosquito larvae in the third to fourth larval stage were then introduced. The temperature was kept at 25° C. The action was assessed after 24 hours.

In this experiment, compound 1.1 was far superior to the comparative substances.

Continuous Contact Action on *Musca domestica* (Housefly)

Both the tops and bottoms of Petri dishes 10 cm in diameter were lined with a total of 2 ml of acetonic solutions of the active ingredients. After the solvent had evaporated (about 30 mins.), 10 flies were introduced into each dish. The kill rate was established after 4 hours.

In this experiment, compound 1.1 was superior to comparative substances I and II.

Contact Action on *Prodenia litura*

Glass Petri dishes 10 cm in diameter were treated with acetonic solutions of the active ingredients. After the solvent had evaporated, 5 caterpillars in the fourth larval stage were introduced and the dishes closed. The kill rate was assessed after 4 hours.

In this experiment, compound 1.1 was superior to comparative substance II. Comparative substance I achieved 0% kill at the higher concentration of 1 mg.

Contact Action on *Plutella maculipennis* (Diamondback Moth)

Leaves of young cabbage plants were dipped for 3 seconds into aqueous emulsions of the active ingredients and placed, after excess liquid had been briefly allowed to drip off, on a moist filter paper in a Petri dish. 10 caterpillars of the fourth stage were placed on each leaf. The kill rate was determined after 48 hours.

In this experiment, compound 1.1 had a 50 times higher activity than comparative substance I.

Contact Action on *Ornithodorus moubata* (Tick)

Young ticks (1.5 to 2 mm in diameter) which had sucked blood once were individually picked up by means of a suction tube. A strong light source drove the active animals from the discarded exoskeleton remains.

5 ticks were placed in paper bags, and the bags were dipped for 5 seconds in aqueous active ingredient formulations. The bags were then suspended and the action was assessed after 48 hours by holding the bags up to a strong light source; the animals still living tried to evade the light and were easy to recognize from their movements.

In this experiment, compound 1.1 had an activity 20 times higher than comparative substance I and 40 times higher than comparative substance II.

We claim:

1. The compound 2'-methyl-3'-phenylbenzyl-3-(2-chloro-2-(4-chlorophenyl)-ethenyl)-2,2-dimethylcyclopropanecarboxylate.

2. The compound trans,Z-2'-methyl-3'phenylbenzyl-3-(2-chloro-2-(4-chlorophenyl)-ethenyl)-2,2-dimethylcyclopropanecarboxylate.

3. The compound having the structural formula:

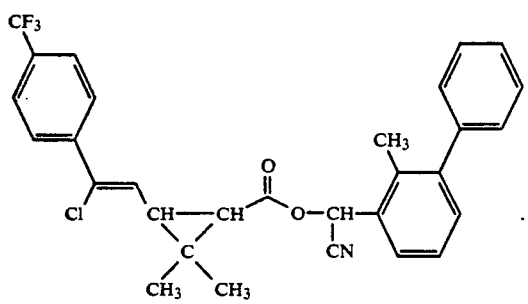

4. A pesticidal composition comprising a pesticide carrier and a pesticidally effective amount of a compound selected from the group consisting of 2'-methyl-3'-phenylbenzyl-3-(2-chloro-2-(4-chlorophenyl)-ethenyl)-2,2-dimethylcyclopropanecarboxylate and a compound having the structural formula:

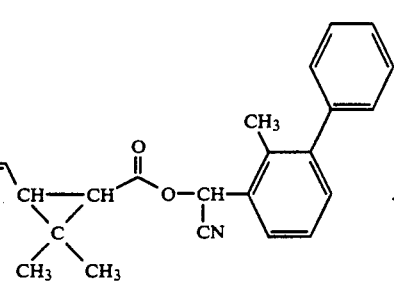

5. A process for combating insects, mites, or nematodes, which comprises applying to the insects, mites, or nematodes or their habitats an effective amount of the composition of claim 4.

* * * * *

UNITED STATES PATENT AND TRADEMARK OFFICE
CERTIFICATE OF CORRECTION

PATENT NO. : 5,066,673
DATED : NOV. 19, 1991
INVENTOR(S) : ZOMBIK et al.

It is certified that error appears in the above-identified patent and that said Letters Patent is hereby corrected as shown below:

On the title page, in the abstract, in the line beginning with "$R^6$":

"(n=1 to 4)," should read --(m=1 to 4),--

On the title page, in the abstract, in the line beginning with "$R^7$":

"p=0 to 25)," should read --(p=0 to 5)--

Signed and Sealed this

Twenty-eighth Day of December, 1993

Attest:

BRUCE LEHMAN

*Attesting Officer*     *Commissioner of Patents and Trademarks*